United States Patent
Robinson et al.

(10) Patent No.: US 6,652,852 B1
(45) Date of Patent: Nov. 25, 2003

(54) CHIMERIC ANTIBODY WITH SPECIFICITY TO HUMAN B CELL SURFACE ANTIGEN

(75) Inventors: Randy R. Robinson, Walnut Creek, CA (US); Alvin Y. Liu, Seattle, WA (US); Jeffrey A. Ledbetter, Seattle, WA (US)

(73) Assignee: Royalty Pharma Finance Trust, Wilimington, DE (US)

( * ) Notice: Subject to any disclaimer, the term of this patent is extended or adjusted under 35 U.S.C. 154(b) by 0 days.

(21) Appl. No.: 09/724,138

(22) Filed: Nov. 28, 2000

Related U.S. Application Data

(63) Continuation of application No. 09/630,198, filed on Aug. 1, 2000, which is a continuation of application No. 09/021,934, filed on Feb. 12, 1998, now Pat. No. 6,120,767, which is a continuation of application No. 08/471,984, filed on Jun. 6, 1995, now Pat. No. 5,721,108, which is a continuation of application No. 07/665,939, filed on Mar. 5, 1991, now Pat. No. 5,500,362, which is a continuation of application No. 07/195,961, filed on May 13, 1988, now abandoned, which is a continuation of application No. 07/016,202, filed on Jan. 8, 1987, now abandoned, which is a continuation-in-part of application No. PCT/US86/02269, filed on Oct. 27, 1986.

(51) Int. Cl.$^7$ ....................... A61K 39/395; C07K 16/00

(52) U.S. Cl. ............................... 424/133.1; 424/153.1; 424/155.1; 424/178.1; 424/182.1; 424/183.1; 530/387.3; 530/388.73; 530/391.1; 530/391.3; 530/391.7

(58) Field of Search ........................... 424/133.1, 153.1, 424/155.1, 178.1, 182.1, 183.1; 530/387.3, 388.73, 391.1, 391.3, 391.7

(56) References Cited

U.S. PATENT DOCUMENTS

| | | |
|---|---|---|
| 4,468,464 A | 8/1984 | Cohen et al. |
| 4,486,538 A | 12/1984 | Bogoch |
| 4,650,756 A | 3/1987 | Old et al. |
| 4,708,862 A | 11/1987 | Baldwin |
| 4,724,212 A | 2/1988 | Epstein |
| 4,724,213 A | 2/1988 | Epstein |
| 4,816,567 A | 3/1989 | Cabilly et al. |
| 4,863,726 A | 9/1989 | Stevens et al. |
| 5,091,178 A | 2/1992 | Hellstrom et al. |
| 5,354,847 A | 10/1994 | Liu et al. |
| 5,500,302 A | 3/1996 | Phillips et al. |
| 5,500,362 A | 3/1996 | Robinson et al. |
| 5,545,403 A | 8/1996 | Page |
| 5,545,404 A | 8/1996 | Page |
| 5,545,405 A | 8/1996 | Page |
| 5,595,721 A | 1/1997 | Kaminski et al. |
| 5,677,180 A | 10/1997 | Robinson et al. |
| 5,721,108 A | 2/1998 | Robinson et al. |
| 5,807,715 A * | 9/1998 | Morrison et al. ......... 435/69.6 |
| 5,843,398 A | 12/1998 | Kaminski et al. |
| 6,015,542 A | 1/2000 | Kaminski et al. |
| 6,090,365 A | 7/2000 | Kaminski et al. |
| 6,120,767 A | 9/2000 | Robinson et al. |

FOREIGN PATENT DOCUMENTS

| | | |
|---|---|---|
| EP | 0 120 694 A2 | 10/1984 |
| EP | 0 125 023 A1 | 11/1984 |
| EP | 0 171 496 A2 | 2/1986 |
| EP | 0 173 494 A2 | 3/1986 |
| EP | 0 184 187 A2 | 6/1986 |
| WO | WO 83/03971 | 11/1983 |
| WO | WO 86/01533 | 3/1986 |
| WO | WO 87/02671 | 5/1987 |
| WO | WO 87/02776 | 5/1987 |
| WO | WO 88/03145 | 5/1988 |

OTHER PUBLICATIONS

Houghton, A.N. et al., "Mouse monoclonal IgG3 antibody detecting $G_{D3}$ ganglioside: A phase I trial in patients with malignant melanoma," *Proc. Natl. Acad. Sci.* 82(4):1242–1246 (Feb. 1985).

Parker, B.A. et al., "Radioimmunotherapy of Human B–Bell Lymphoma with $^{90}$Y–conjugated Antiidiotype Monoclonal Antibody," *Cancer Research (Suppl.)* 50(3):1022s–1028s (Feb. 1990).

Harrison's Principles of Internal Medicine, $9^{th}$ Edition, Eds. Isselbacher, K.J. et al., Chapter 324: Principles of Cancer Therapy, pp. 1600–1601 and 1613 (1980).

Barr, I.G. et al., "Retargeting of Cytolytic T Lymphocytes by Heteroaggregated (Bispecific) Antibodies," *Cancer Detection and Prevention* 12:439–450 (1988).

Clark, E.A. et al., "Activation of Human B Cells Mediated Through Distinct Cell Surface Differentiation Antigens, Bp35 and Bp50," *Proc. Natl. Acad. Sci. USA* 83:4494–4498 (Jun. 1986).

European Search Report for EPO Application No. EP 115769.9 (Feb. 1988).

Bodmer, M.W., "Recombinant Antibodies for Clinical Use," *Abstracts of Oral Presentations,* p. 526 (1986).

Boulianne, G.L. et al., "Production of Functional Chimaeric Mouse/Human Antibody," *Nature* 312:643–646 (Dec. 1984).

Brown, B.A. et al., "Tumor–Specific Genetically Engineered Murine/Human Chimeric Monoclonal Antibody," *Cancer Research* 47:3577–3583 (Jul. 1987).

Brüggemann, M. et al., "Comparison of the Effector Functions of Human Immunoglobulins Using a Matched Set of Chimeric Antibodies," *J. Exp. Med.* 166:1351–1361 (Nov. 1987).

Cabilly, S. et al., "Generation of Antibody Activity from Immunoglobulin Polypeptide Chains Produced in *Escherichia coli,*" *Proc. Natl. Acad. Sci. USA* 81:3273–3277 (Jun. 1984).

Clark, E.A. et al., "Role of the Bp35 Cell Surface Polypeptide in Human B–cell Activation," *Proc. Natl. Acad. Sci. USA* 82:1776–1770 (Mar. 1985).

(List continued on next page.)

*Primary Examiner*—David Saunders
(74) *Attorney, Agent, or Firm*—Testa, Hurwitz & Thibeault, LLP

(57) ABSTRACT

A chimeric antibody with human constant region and murine variable region, having specificity to a 35 kDA polypeptide (Bp35(CD20)) expressed on the surface of human B cells, methods of production, and uses.

30 Claims, 10 Drawing Sheets

OTHER PUBLICATIONS

Clark, E.A. et al., Abstract 0147—"Anti–Bp35 Antibody Induces Human B Cell Proliferation: Implications for In Vivo Immunotherapy," *Journal of Cellular Biochemistry (Supplement 9A)*, p. 63 (Jan./Feb. 1985).

Gillies, S.D. et al., "Expression of Genetically Engineered Immunoconjugates of Lymphotoxin and a Chimeric Anti–Ganglioside GD2 Antibody," *Hybridoma* 10(3):347–356 (Jan. 1991).

Hellstrom et al. in Baldwin et al., "Monoclonal Antibodies for Cancer Detection and Therapy," *Academic Press, New York*, pp. 34–36 (1985).

International Search Report for PCT Publication No. 88/03145 (Feb. 1988).

Jones, P.T. et al., "Replacing the Complementarity–Determining Regions in a Human Antibody with those from a Mouse," *Nature* 321:522–525 (May/Jun. 1986).

Liu, A.Y. et al., "Chimeric Mouse–Human IgG1 Antibody that can Mediate Lysis of Cancer Cells," *Proc. Natl. Acad. Sci., USA* 84:3439–3443 (May 1987).

Liu, A.Y. et al., "Production of a Mouse–Human Chimeric Monoclonal Antibody to CD20 with Potent Fc–Dependent Biologic Activity," *J. Immunol.* 139:3521–3526 (Nov. 1987).

Marx, J.L., "Antibodies Made to Order," *Science* 229:455–456 (Aug. 1985).

Morrison, S.L. et al., "Chimeric Human Antibody Molecules: Mouse Antigen–Binding Domains with Human Constrant Region Domains," *Proc. Natl. Acad. Sci., USA* 81:6851–6855 (Nov. 1984).

Morrison, S.L. et al., "Transfectomas Provide Novel Chimeric Antibodies," *Science* 229:1202–1207 (Sep. 1985).

Mujoo, K. et al., "A potent and specific immunotoxin for tumor cells expressing disialoganglioside $GD_2$," *Cancer Immunology Immunotherapy* 34: 198–204 (1991).

Nadler, L.M. et al., "A Unique Cell Surface Antigen Identifying Lymphoid Malignancies of B Cell Origin," *J. Clin. Invest.* 67:134–140 (Jan. 1981).

Neuberger, M.S., "Making Novel Antibodies by Expressing Transfected Immunoglobulin Genes," *TIBS*, 347–349 (Sep. 1985).

Neuberger, M.S., "A Hapten–Specific Chimaeric IgE Antibody with Human Physiological Effector Function," *Nature* 314:268–270 (Mar. 1985).

Neuberger, M.S., "Recombinant Antibodies Possessing Novel Effector Functions," *Nature* 312:604–608 (Dec. 1984).

Nishimura Y. et al., "Recombinant Human–House Chimeric Monoclonal Antibody Specific for Common Acute Lymphocytic Leukemia Antigen," *Canc. Res.* 47:999–1005 (Feb. 1987).

Nose, M. et al., "Biological Significance of Carbohydrate Chains on Monoclonal Antibodies," *Proc. Natl. Acad. Sci., USA* 80:6632–6636 (Nov. 1983).

Oi, V.T. et al., "Chimeric Antibodies," *BioTechniques* 4:214–221 (May/Jun. 1986).

Press, O. et al., Abstract 864—"Serotherapy of Malignant B Cell Lymphomas with Monoclonal Antibody IF5 (ANTI–CD20)," *Twenty–Second Annual Meeting of the American Society of Clinical Oncology* 5:221 (Mar. 1986).

Robinson, R.R. et al., "Chimeric mouse–human anti–carcinoma antibodies that mediate different anti–tumor cell biological activities," *Hum. Antibod. Hybridomas* 2:84–93 (Apr. 1991).

Roit, I.M., "Essential Immunology," Blackwell Scientific Publications, Oxford, U.K., p. 165 (1984).

Sahagan, B.G. et al., "A Genetically Engineered Murine/Human Chimeric Antibody Retains Specificity for Human Tumor–Associated Antigen," *J. Immunol.* 137:1066–1074 (Aug. 1986).

Stashenko, P. et al., "Characterization of a Human B Lymphocyte–Specific Antigen," *J. Immunol.* 125:1678–1685 (Oct. 1980).

Steplewski, Z. et al., "Biological Activity of Human–Mouse IgG1, IgG2, IgG3, and IgG4 Chimeric Monoclonal Antibodies with Antitumor Specificity," *Proc. Natl. Acad. Sci. USA* 85:4852–4856 (Jul. 1988).

Sun, L.K. et al., "Chimeric Antibody with Human Constant Regions and Mouse Variable Regions Directed Against Carcinoma–Associated Antigen 17–1A," *Proc. Natl. Acad. Sci., USA* 84:214–218 (Jan. 1987).

Sun, L.K. et al., "Chimeric Antibodies with 17–1A Derived Variable and Human Constant Regions," *Hybridoma* 5 Supp. 1:17–20 (Apr. 1986).

Takeda, S. et al., "Construction of Chimaeric Processed Immunoglobulin Genes Containing Mouse Variable and Human Constant Region Sequences," *Nature* 314: 452–454 (Apr. 1985).

Tan, L.K. et al., "A Human–Mouse Chimeric Immunoglobulin Gene with a Human Variable Region is Expressed in Mouse Myeloma Cells," *J. Immunol.* 135:3564–3567 (Nov. 1985).

Walker, C. et al., "Activation of T cells by cross–linking an anti–CD3 antibody with a second anti–T cell antibody: mechanism and subset–specific activation," *Eur. J. Immunol.* 17(6):873–880 (Jun., 1987).

Williams, G.T. et al., "Production of Antibody–Tagged Enzymes by Myeloma Cells: Application to DNA Polymerase I Klenow," *Gene* 43:319–324 (1986).

Wood, C.R. et al., "The Synthesis and In Vivo Assembly of Functional Antibodies in Yeast," *Nature* 314:446–449 (Apr. 1985).

IDEC Pharmaceuticals Corp. and Genentech, Inc., Product Sheet for Rituxan® (1998).

Munro, "Uses of chimeric antibodies," *Nature*, 312:597 (Dec. 13, 1984).

Dickson, "Scientists Produce Chimeric Monoclonal Abs.," *Genetic Engineering News*, 5(3), p. 1 and p. 33.

Alexander, A. et al., "γ heavy chain disease in man: cDNA sequence supports partial gene deletion model," *Proc. Natl. Acad. Sci. USA*, 79:3260–3264 (1982).

Dolby, T.W. et al., "Cloning and partial nucleotide sequence of human Immunoglobulin μ chain cDNA from B cells and mouse–human hybridomas," *Proc. Natl. Acad. Sci. USA*, 77:6027–6031 (1980).

Seno, M. et al., "Molecular cloning and nucleotide sequencing of human immunoglobulin ϵ chain cDNA," *Nucleic Acids Research*, 11:719–726 (1983).

Kurokawa, T. et al., "Expression of human immunoglobulin E ϵ chain cDNA in *E. coli*," *Nucleic Acids Research*, 11:3077–3085 (1983).

Liu, F.T. et al., "Expression of a biologically active fragment of human IgE ϵ chain in *Escherichia coli*," *Proc. Natl. Acad. Sci. USA*, 81:5369–5373 (Sep. 1984).

Tsujimoto, Y. et al., "Molecular cloning of a human immunoglobulin γ chain variable sequence," *Nucleic Acids Res.*, 12:8407–8414 (Nov. 1984).

Brunt, "There's Noting (Quite) Like the Real Thing," *Biotechnology,* 4:835, 839 (1986).

Hellström et al., "Antitumor effects of L6, and IgG2a antibody that reacts with most human carcinomas," *Proc. Natl. Acad. Sci. USA,* 83:7059–7063 (1986).

Press et al., "Monoclonal Antibody IF5 (Anti–CD20) Serotherapy of Human B Cell Lymphomas," *Blood,* 69(2):584–591 (1987).

Roitt, "Essential Immunology," Blackwell Scientific Publications, Oxford, U.K., pp. 242–243 (1984).

Levy et al., "Tumor Therapy with Monoclonal Antibodies," Federation Proceedings, 42:2650–2656 (1983).

See–Lasley et al., "Manual of Oncology Therapeutics," The C.V. Mosby Company, St. Louis, MO, pp. 44–71 (1981).

* cited by examiner

Ig heavy chain J-C region
human heavy chain J regions                                                J  |CH1
JH1       GCTGAATACTTCCAGCACTGGGGCCAGGGCACCCTGGTCACCGTCTCCTCAG
JH2       CTACTGGTACTTCGATCTCTGGGGCCGTGGCACCCTGGTCACTGTCTCCTCAG
JH3         ATGCTTTTGATGTCTGGGGCCAAGGGACAATGGTCACCGTCTCTTCAG
JH4        ACTACTTTGACTACTGGGGCCAAGGAACCCTGGTCACCGTCTCCTCAG
JH5       ACACTGGTTCGACTCCTGGGGCCAAGGAACCCTGGTCACCGTCTCCTCAG
JH6    AT (TAC)$_5$ GGTATGGACGTCTGGGGGCAAGGGACCACGGTCACCGTCTCCTCAG
Consensus         TCGACCTCTGGGGCCAAGGAACCCTGGTCACCGTCTCCTCAG mouse heavy chain J regions                                                J  |CH1
JH1       TACTGGTACTTCGATGTCTGGGGCGCAGGGACCACGGTCACCGTCTCCTCAG
JH2          TACTTTGACTACTGGGGCCAAGGCACCACTCTCACAGTCTCCTCAG
JH3        CCTGGTTTGCTTACTGGGGCCAAGGGACTCTGGTCACTGTCTCTGCAG
JH4       TACTATGCTATGGACTACTGGGGTCAAGGAACCTCAGTCACCGTCTCCTCAG
Consensus        TTTGACTACTGGGGCCAAGGGACCACGGTCACCGTCTCCTCAG Ig light chain J-C region
human Kappa J region                                                       J  |C
JK1       GGACGTTCGGCCAAGGGACCAAGGTGGAAATCAAAC
JK2       ACACTTTTGGCCAGGGGACCAAGCTGGAGATCAAAC
JK3       TCACTTTCGGCCCTGGGACCAAAGTGGATATCAAAC
JK4       TCACTTTCGGCGGAGGGACCAAGGTGGAGATCAAAC
JK5       TCACCTTCGGCCAAGGGACACGACTGGAGATTAAAC
Consensus       TTCGGCCAAGGGACCAAGGTGGAGATCAAAC mouse Kappa J region                                                       J  |C
JK1       TGGACGTTCGGTGGAGGCACCAAGCTGGAAATCAAAC
JK2       TACACGTTCGGAGGGGGGACCAAGCTGGAAATAAAAC
JK3       TTCACATTCAGTGATGGACCAGACTGGAAATAAAAC
JK4       TTCACGTTCGGCTCGGGGACAAAGTTGGAAATAAAAC
JK5       CTCACGTTCGGTGCTGGGACCAAGCTGGAGCTGAAAC
Consensus       TTCGGTGGGGGGACCAAGCTGGAAATAAAAC
UIG [MJK]         $_3$,TGGTTCGACCTTTATTTTG$_{5'}$ human Lambda pseudo J region                                               J  |C
JPSL1     CACATGTTTGGCAGCAAGACCCAGCCCACTGTCTTAG mouse Lambda J region                                                      J  |C
JL1       TGGGTGTTCGGTGGAGGAACCAAACTGACTGTCCTAG
JL2       TATGTTTTCGGCGGTGGAACCAAGGTCACTGTCCTAG
JL3       TTTATTTTCGGCAGTGGAACCAAGGTCACTGTCCTAG
Consensus       TTCGGCGGTGGAACCAAGGTCACTGTCCTAG

FIG. 2 mouse heavy chain J segments

```
JH1  T A C T G G T A C T T C G A T G T C T G G G G C G C A G G G A C C A C G G T C A C C G T C T C C T C A
JH2              T A C T T T G A C T A C T G G G G C C A A G G C A C C A C T C T C A C A G T C T C C T C A
JH3  C C T G G T T T G C T T A C T G G G G C C A A G G G A C T C T G G T C A C T G T C T C T G C A
JH4  T A C T A T G C T A T G G A C T A C T G G G G T C A A G G A A C C T C A G T C A C C G T C T C C T C A
``` consensus primer: UIGH
AGGGACCAC GGTCACCGTCTC
→ Bst EII

FIG. 3A mouse κ light chain J segments

```
JK1  T G G A C G T T C G G T G G A G G C A C C A A G C T G G A A A T C A A A A
JK2  T A C A C G T T C G G A G G G G G G A C C A A G C T G G A A A T A A A A A
JK4  T T C A C G T T C G G C T C G G G G A C A C C A A G T C T G G A A A T A A A A
JK5  C T C A C G T T C G G T G C T G G G A C C A A G C T G G A G C T G A A A
``` consensus primer: UIGκ
GGGACC AAGCTT GAG
→ Hind III

FIG. 3B pGMH6 Human Cγ1 constant domain module $J_H$

G GTC ACC GTC TCT TCA | GCC TCC ACC AAG GGC CCA TCG GTC TTC-
↑                                                ↑
Bst EII                                          ApaI

FIG. 4A pGML60 Human Cκ constant domain module $J_\kappa 4$

GAT CAT CTC CCT CTC ACT TTC GGC GGA GGG ACC AAG GTG GAG ATG AAA|-
                              —————————C-T——— $J_\kappa$Hind III
                                      ↑
                                   Hind III

FIG. 4B

2H7 HEAVY CHAIN VARIABLE SEQUENCE

```
                                                              leader
                                       met gly phe ser arg ile phe
C₃₃GTACCTCTCTACAGTCCCTGAAGACACTGACTCTAACCATG GGA TTC AGC AGG ATC TTT
                                     ↑NcoI-SalI peptide                                FRI
                                         |  °   °    °   °   °
leu phe leu leu ser val thr thr gly val his ser gln ala lyr leu gln
CTC TTC CTC CTG TCA GTA ACT ACA GGT GTC CAC TCC CAG GCT TAT CTA CAG °   °   °   °   °   °   °
gln ser gly ala glu leu val arg pro gly ala ser val lys met ser cys
CAG TCT GGG GCT GAG CTG GTG AGG CCT GGG GCC TCA GTG AAG ATG TCC TGC FR1│CDR1             CDR1│FR2
lys ala ser gly tyr thr phe thr ser tyr asn met his trp val lys gln
AAG GCT TCT GGC TAC ACA TTT ACC AGT TAC AAT ATG CAC TGG GTA AAG CAG FR2│CDR2
thr pro arg gln gly leu glu trp ile gly ala ile tyr pro gly asn gly
ACA CCT AGA CAG GGC CTG GAA TGG ATT GGA GCT ATT TAT CCA GGA AAT GGT CDR2│FR3
asp thr ser tyr asn gln lys phe lys gly lys ala thr leu thr val asp
GAT ACT TCC TAC AAT CAG AAG TTC AAG GGC AAG GCC ACA CTG ACT GTA GAC lys ser ser ser thr ala̅ tyr met gln leu ser ser leu thr ser glu asp
AAA TCC TCC AGC ACA GCC TAC ATG CAG CTC AGC AGC CTG ACA TCT GAA GAC FR3│CDR3
ser ala val tyr phe cys ala arg val val tyr tyr ser asn ser tyr trp
TCT GCG GTC TAT TTC TGT GCA AGA GTG GTG TAC TAT AGT AAC TCT TAC TGG
─────────────────────── J_H1 ────────────────────── DSP2
        CDR3│FR4                                    FR4
tyr phe asp val trp gly thr gly thr thr val thr val ser
TAC TTC GAT GTC TGG GGC ACA GGG ACC ACG GTC ACC GTC TCG₃₀
                            ↑BstEII     J_HBstEII primer
```

FIG. 5

2H7 LIGHT CHAIN VARIABLE SEQUENCE

```
                                                        leader peptide
                              met asp phe gln val gln ile phe ser phe leu leu
C23CCCAAAATTCAAAGACAAATG GAT TTT CAA GTG CAG ATT TTC AGC TTC CTG CTA
       ——GTC———— SalI primer
                                                |FR1
ile ser ala ser val ile ile ala arg gly gln ile val leu ser gln ser
ATC AGT GCT TCA GTC ATA ATT GCC AGA GGA CAA ATT GTT CTC TCC CAG TCT FR1 |
pro ala ile leu ser ala ser pro gly glu lys val thr met thr cys arg
CCA GCA ATC CTG TCT GCA TCT CCA GGG GAG AAG GTC ACA ATG ACT TGC AGG CDR1                             CDR1| FR2
ala ser ser ser val ser tyr met his trp tyr gln gln lys pro gly ser
GCC AGC TCA AGT GTA AGT TAC ATG CAC TGG TAC CAG CAG AAG CCA GGA TCC
                                         KpnI↑              ↑BamHI
              FR2| CDR2                         CDR2| FR3
ser pro lys pro trp ile tyr ala pro ser asn leu ala ser gly val pro
TCC CCC AAA CCC TGG ATT TAT GCC CCA TCC AAC CTG GCT TCT GGA GTC CCT ala arg phe ser gly ser gly ser gly thr ser tyr ser leu thr ile ser
GCT CGC TTC AGT GGC AGT GGG TCT GGG ACC TCT TAC TCT CTC ACA ATC AGC FR3|CDR3
              o   o   o   o   o   o   o   o   o   o   o   o
arg val glu ala glu asp ala ala thr tyr tyr cys gln gln trp ser phe
AGA GTG GAG GCT GAA GAT GCT GCC ACT TAT TAC TGC CAG CAG TGG AGT TTT
                                          ——JK5——
          CDR3|FR4                                       FR4
   o   o   o   o   o   o   o   o
asn pro pro thr phe gly ala gly thr lys leu glu leu lys
AAC CCA CCC ACG TTC GGT GCT GGG ACC AAG CTG GAG CTG AAA
                              ————T——JKHindIII primer
```

FIG. 6

CHIMERIC ANTIBODY WITH SPECIFICITY TO HUMAN B CELL SURFACE ANTIGEN

The present application is a continuation of U.S. Ser. No. 09/630,198, filed on Aug. 1, 2000, which is a continuation of U.S. Ser. No. 09/021,934, filed on Feb. 12, 1998, now U.S. Pat. No. 6,120,767, which is a continuation of U.S. Ser. No. 08/471,984, filed Jun. 6, 1995, now U.S. Pat. No. 5,721,108, which is a continuation of U.S. Ser. No. 07/665,939, filed Mar. 5, 1991, now U.S. Pat. No. 5,500,362, which is a continuation of U.S. Ser. No. 07/195,961, filed May 13, 1988, now abandoned, which is a continuation of U.S. Ser. No. 07/016,202, filed Jan. 8, 1987, now abandoned, which is a continuation-in-part of international patent application serial number PCT/US86/02269, filed Oct. 27, 1986, which was published under PCT Article 21(2) in English. The entire disclosures of U.S. Ser. No. 09/630,198, U.S. Ser. No. 09/021,934, U.S. Ser. No. 08/471,984, U.S. Ser. No. 07/665,939, U.S. Ser. No. 07/195,961, and U.S. Ser. No. 07/016,202, are incorporated herein by reference.

BACKGROUND OF THE INVENTION

1. Field of the Invention

This invention relates to recombinant DNA methods of preparing an antibody with specificity for an antigen on the surface of human B cells, genetic sequences in coding therefor, as well as methods of obtaining such sequences.

2. Background Art

The application of cell-to-cell fusion for the production of monoclonal antibodies by Kohler and Milstein (Nature (London), 256: 495, 1975) spawned a revolution in biology equal in impact to that from the invention of recombinant DNA cloning. Monoclonal antibodies produced from hybridomas are already widely used in clinical and basic scientific studies. Applications of human monoclonal antibodies produced by human hybridomas hold great promise for the treatment of cancer, viral and microbial infections, certain immunodeficiencies with diminished antibody production, and other diseases and disorders of the immune system.

Unfortunately, a number of obstacles exist with respect to the development of human monoclonal antibodies. This is especially true when attempting to develop therapeutically useful monoclonal antibodies which define human cell surface antigens. Many of these human cell surface antigens are not recognized as foreign antigens by the human immune system; therefore, these antigens are not immunogenic in man. By contrast, human cellular antigens which are immunogenic in mice can be used for the production of mouse imonoclonal antibodies that specifically recognize the human antigens. Although such antibodies may be used therapeutically in man, repeated injections of "foreign" antibodies, such as a mouse antibody, in humans, can lead to harmful hypersensitivity reactions as well as increased rate of clearance of the circulating antibody molecules so that the antibodies do not reach their target site. Furthermore, mouse monoclonal antibodies may lack the ability to efficiently interact with human effector cells as assessed by functional assays such as antibody-dependent cellular cytotoxicity (ADCC) and complement-mediated cytolysis (CDC).

Another problem faced by immunologists is that most human monoclonal antibodies obtained in cell culture are of the IgM type. When it is desirable to obtain human monoclonals of the IgG type, however, it has been necessary to use such techniques as cell sorting to identify and isolate the few cells which are producing antibodies of the IgG or other type from the majority producing antibodies of the IgM type.

A need therefore exists for an efficient method of switching antibody classes, for any given antibody of a predetermined or desired antigenic specificity.

The present invention bridges both the hybridoma and genetic engineering technologies to provide a quick and efficient method, as well as products derived therefrom, for the production of a chimeric human/non-human antibody.

The chimeric antibodies of the present invention embody a combination of the advantageous characteristics of monoclonal antibodies derived from mouse-mouse hybridomas and of human monoclonal antibodies. The chimeric monoclonal antibodies, like mouse monoclonal antibodies, can recognize and bind to a human target antigen; however, unlike mouse monoclonal antibodies, the species-specific properties of the chimeric antibodies will avoid the induction of harmful hypersen-sitivity reactions and may allow for resistance to clearance when used in humans in vivo. Also, the inclusion of appropriate human immunoglobulin sequences can result in an antibody which efficiently interacts with human effector cells in vivo to cause tumor cell lysis and the like. Moreover, using the methods disclosed in the present invention, any desired antibody isotype can be conferred upon a particular antigen combining site.

INFORMATION DISCLOSURE STATEMENT

Approaches to the problem of producing chimeric antibodies have been published by various authors.

\* Note: The present Information Disclosure Statement is subject to the provisions of 37 C.F.R. 1.97(b). In addition, Applicants reserve the right to demonstrate that their invention was made prior to any one or more of the mentioned publications.

Morrison, S. L. et al., *Proc. Natl. Acad. Sci., USA*, 81: 6851–6855 (November 1984), describe the production of a mouse-human antibody molecule of defined antigen binding specificity, produced by joining the variable region genes of a mouse antibody-producing myeloma cell line with known antigen binding specificity to human immunoglobulin constant region genes using recombinant DNA techniques. Chimeric genes were constructed, wherein the heavy chain variable region exon from the myeloma cell line S107 well joined to human IgG1 or IgG2 heavy chain constant region exons, and the light chain variable region exon from the same myeloma to the human kappa light chain exon. These genes were transfected into mouse myeloma cell lines and. Transformed cells producing chimeric mouse-human antiphosphocholine antibodies were thus developed.

Morrison, S. L. et al., European Patent Publication No. 173494 (published Mar. 5, 1986), disclose chimeric "receptors" (e.g. antibodies) having variable regions derived from one species and constant regions derived from another. Mention is made of utilizing cDNA cloning to construct the genes, although no details of cDNA cloning or priming are shown. (see pp 5, 7 and 8).

Boulianne, G. L. et al., *Nature*, 312: 643 (Dec. 13, 1984), also produced antibodies consisting of mouse variable regions joined to human constant regions. They constructed irmmiunoglobulin genes in which the DNA segments encoding mouse variable regions specific for the hapten trinitrophenyl (TNP) were joined to segments encoding human mu and kappa constant regions. These chimeric genes were expressed as functional TNP binding chimeric IgM.

For a commentary on the work of Boulianne et al. and Morrison et al., see Munro, *Nature*, 312: 597 (Dec. 13, 1984), Dickson, *Genetic Engineering News*, 5, No. 3 (March 1985), or Marx, *Science*, 229: 455 (August 1985).

Neuberger, M. S. et al., *Nature*, 314: 268 (Mar. 25, 1985), also constructed a chimeric heavy chain immunoglobulin gene in which a DNA segment encoding a mouse variable region specific for the hapten 4-hydroxy-3-nitrophenacetyl (NP) was joined to a segment encoding the human epsilon region. When this chimeric gene was transfected into the J558L cell line, an antibody was produced which bound to the NP hapten and had human IgE properties.

Neuberger, M. S. et al., have also published work showing the preparation of cell lines that secrete hapten-specific antibodies in which the Fc portion has been replaced either with an active enzyme moiety (Williams, G. and Neuberger, M. S. *Gene* 43:319, 1986) or with a polypeptide displaying c-myc antigenic determinants (*Nature*, 312:604, 1984).

Neuberger, M. et. al., PCT Publication WO 86/01533, (published Mar. 13, 1986) also disclose production of chimeric antibodies (see p. 5) and suggests, among the technique's many uses the concept of "class switching" (see p. 6).

Taniguchi, M., in European Patent, Publication No. 171 496 (published Feb. 19, 1986) discloses the production of chimeric antibodies having variable regions with tumor specificty derived from experimental animals, and constant regions derived from human. The corresponding heavy and light chain genes are produced in the genomic form, and expressed in mammalian cells.

Takeda, S. et al., *Nature*, 314: 452 (Apr. 4, 1985) have described a potential method for the construction of chimeric immunoglobulin genes which have intron sequences removed by the use of a retrovirus vector. However, an unexpected splice donor site caused the deletion of the V region leader sequence. Thus, this approach did not yield complete chimeric antibody molecules.

Cabilly, S. et al., *Proc. Natl. Acad. Sci., USA*, 81: 3273–3277 (June 1984), describe plasmids that direct the synthesis in *E. coli* of heavy chains and/or light chains of anti-carcinoembryonic antigen (CEA) antibody. Another plasmid was constructed for expression of a truncated form of heavy chain (Fd') fragment in *E. coli*. Functional CEA-binding activity was obtained by in vitro reconstitution, in *E. coli* extracts, of a portion of the heavy chain with light chain.

Cabilly, S., et al., European Patent Publication 125023 (published Nov. 14, 1984) describes chimeric immunoglobulin genes and their presumptive products as well as other modified forms. On pages 21, 28 and 33 it discusses cDNA cloning and priming.

Boss, M. A., European Patent Application 120694 (published Oct. 3, 1984) shows expression in *E. coli* of non-chimeric immunoglobulin chains with 4-nitrophenyl specificity. There is a broad description of chimeric antibodies but no details (see p. 9).

Wood, C. R. et al., *Nature*, 314: 446 (April, 1985) describe plasmids that direct the synthesis of mouse anti-NP antibody proteins in yeast. Heavy chain mu antibody proteins appeared to be glycosylated in the yeast cells. When both heavy and light chains were synthesized in the same cell, some of the protein was assembled into functional antibody molecules, as detected by anti-NP binding activity in soluble protein prepared from yeast cells.

Alexander, A. et al., *Proc. Nat. Acad. Sci. USA*, 79: 3260–3264 (1982), describe the preparation of a cDNA sequence coding for an abnormally short human Ig gamma heavy chain (OMM gamma$^3$ HCD serum protein) containing a 19-amino acid leader followed by the first 15 residues of the V region. An extensive internal deletion removes the remainder of the V and the entire $C_H1$ domain. This is cDNA coding for an internally deleted molecule.

Dolby, T. W. et al., *Proc. Natl. Acad. Sci., USA*, 77: 6027–6031 (1980), describe the preparation of a cDNA sequence and recombinant plasmids containing the same coding for mu and kappa human immunoglobulin polypeptides One of the recombinant DNA molecules contained codons for part of the $CH_3$ constant region domain and the entire 3' noncoding sequence.

Seno, M. et al., *Nucleic Acids Research*, 11: 719–726 (1983), describe the preparation of a cDNA sequence and recombinant plasmids containing the same coding for part of the variable region and all of the constant region of the human IgE heavy chain (epsilon chain).

Kurokawa, T. et al., *ibid*, 11: 3077–3085 (1983), show the construction, using cDNA, of three expression plasmids coding for the constant portion of the human IgE heavy chain.

Liu, F. T. et al., *Proc. Nat. Acad. Sci., USA*, 81: 5369–5373 (September 1984), describe the preparation of a cDNA sequence and recombinant plasmids containing the same encoding about two-thirds of the $CH_2$, and all of the $C_H3$ and $C_H4$ domains of human IgE heavy chain.

Tsujimoto, Y. et al., *Nucleic Acids Res.*, 12: 8407–8414 (November 1984), describe the preparation of a human V lambda cDNA sequence from an Ig lambda-pro-duicing human Burkitt lymphoma cell line, by taking advantage of a cloned constant region gene as a primer for cDNA synthesis.

Murphy, J., PCT Publication WO 83/03971 (published Nov. 24, 1983) discloses hybrid proteins made of fragments comprising a toxin and a cell-specific ligand (which is suggested as possibly being an antibody).

Tan, et al., *J. Immunol.* 135:8564 (November, 1985), obtained expression of a chimeric human-mouse immunoglobulin genomic gene after transfection into mouse myeloma cells.

Jones, P. T., et al., *Nature* 321:552 (May 1986) constructed and expressed a genomic construct where CDR domains of variable regions from a mouse monolonal antibody were used to substitute for the. corresponding domains in a human antibody.

Sun, L.K., et al., *Hybridoma* 5 suppl. 1 S17 (1986), describes a chimeric human/mouse antibody with potential tumor specificty. The chimeric heavy and light chain genes are genomic constructs and expressed in mammalian cells.

Sahagan et al., *J. Immun.* 137:1066–1074 (August 1986) describe a chimeric antibody with specificity to a human tumor associated antigen, the genes for which are assembled from genomic sequences.

For a recent review of the field see also Morrison, S. L., *Science* 229: 1202–1207 (Sep. 20, 1985) and Oi, V. T., et al., *BioTechniques* 4:214 (1986).

The Oi, et al., paper is relevant as it argues that the production of chimeric antibodies from cDNA constructs in yeast and/or bacteria is not necessarily advantageous.

See also Commentary on page 835 in *Biotechnology* 4 (1986).

SUMMARY OF THE INVENTION

The invention provides a genetically engineered chimeric antibody of desired variable region specificity and constant region properties, through gene cloning and expression of light and heavy chains. The cloned immunoglobulin gene products can be produced by expression in genetically engineered cells.

The application of oligodeoxyribonucleotide synthesis, recombinant DNA cloning, and production of specific immunoglobulin chains in various prokaryotic and eukaryotic cells provides a means for the large scale production of a chimeric human/mouse monoclonal antibody with specificity to a human B cell surface antigen.

The invention provides cDNA sequences coding for immunoglobulin chains comprising a constant human region and a variable, non-human, region. The immiunoglobulin chains can be either heavy or light.

The invention provides gene sequences coding for immunoglobulin chains comprising a cDNA variable region of the desired specificity. These can be combined with genomic constant regions of human origin.

The invention provides sequences as above, present in recombinant DNA molecules in vehicles such as plasmid vectors, capable of expression in desired prokaryotic or eukaryotic hosts.

The invention provides hosts capable of producing, by culture, the chimeric antibodies and methods of using these hosts.

The invention also provides individual chimeric immunoglobulin individual chains, as well as complete assembled molecules having human constant regions and variable regions with a human B cell surface antigen specificity, wherein both variable regions have the same binding specificity.

Among other immunoglobulin chains and/or molecules provided by the invention are:

(a) a complete functional, immunoglobulin molecule comprising:
   (i) two identical chimeric heavy chains comprising a variable region with a human B cell surface antigen specificity and human constant region and
   (ii) two identical all (i.e. non-chimeric) human light chains.

(b) a complete, functional, immunoglobulin molecule comprising:
   (i) two identical chimeric heavy chains comprising a variable region as indicated, and a human constant region, and
   (ii) two identical all (i.e. non-chimeric) non-human light chains.

(c) a monovalent antibody, i.e., a complete, functional immunoglobulin molecule comprising:
   (i) two identical chimeric heavy chains comprising a variable region as indicated, and a human constant region, and
   (ii) two different light chains, only one of which has the same specificity as the variable region of the heavy chains. The resulting antibody molecule binds only to one end thereof and is therefore incapable of divalent binding.

Genetic sequences, especially cDNA sequences, coding for the aforementioned combinations of chimeric chains or of non-chimeric chains are also provided herein.

The invention also provides for a genetic sequence, especially a cDNA sequence, coding for the variable region of desired specificity of an antibody molecule heavy and/or light chain, operably linked to a sequence coding for a polypeptide different than an immunoglobulin chain (e.g., an enzyme). These sequences can be assembled by the methods of the invention, and expressed to yield mixed-function molecules.

The use of cDNA sequences is particularly advantageous over genomic sequences (which contain introns), in that cDNA sequences can be expressed in bacteria or other hosts which lack appropriate RNA splicing systems.

BRIEF DESCRIPTION OF THE FIGURES

FIG. 2 shows the known nucleotide sequences of human and mouse J regions. Consensus sequences for the J regions are shown below the actual sequences.

Figure 1:
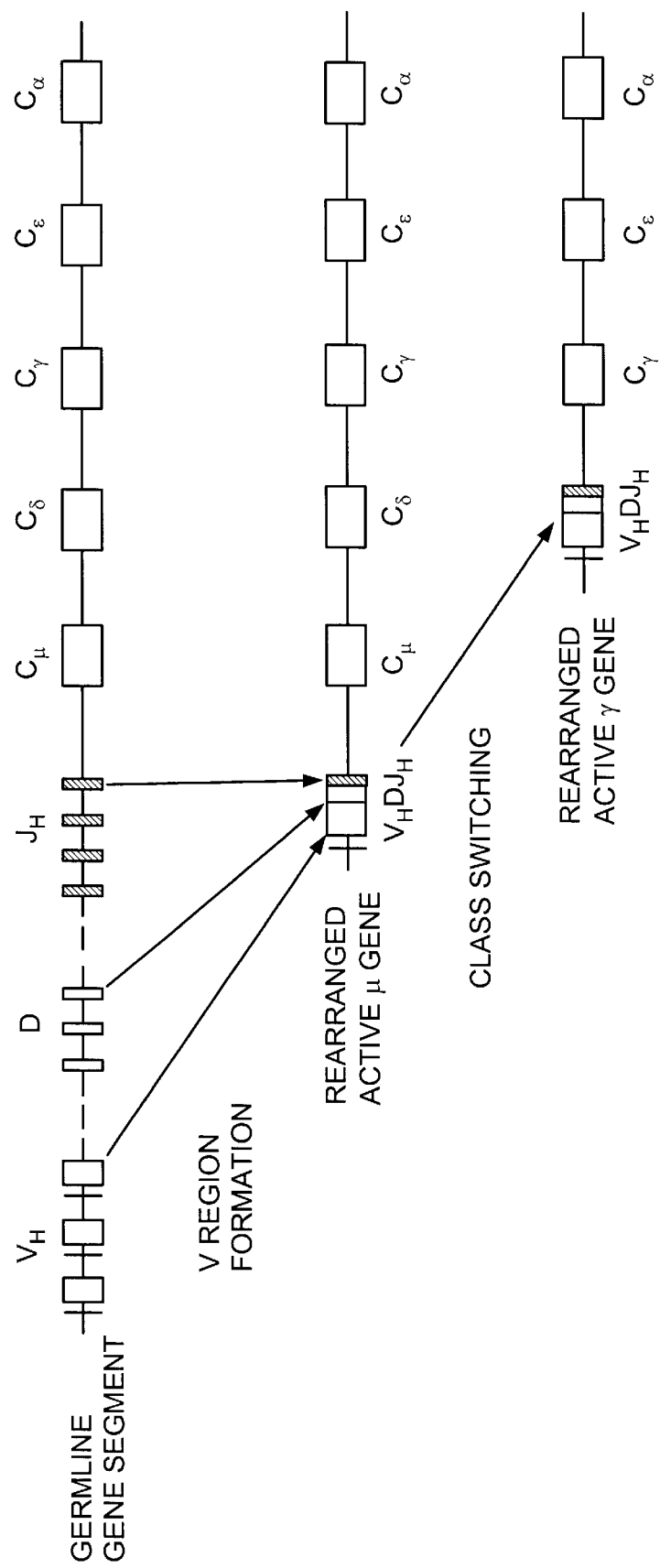
FIG. 1 shows the DNA rearrangements and the expression of immunoglobulin mu and gamma heavy chain genes. This is a schematic representation of the human heavy chain gene complex (not shown to scale). the proper joining of $V_H$, D and $J_H$ gene segments. Heavy chain variable V region formation occurs through This generates an active mu gene. A different kind of DNA rearrangement called "class switching" relocates the joined $V_H$, D and $J_H$ region from the vicinity of mu constant C region to that of another heavy chain C region (switching to gamma is diagrammed here).

The nucleotide sequence of human heavy chain J region JH1 is set forth in SEQ ID NO: 1; that of human heavy chain J region JH2 in SEQ ID NO: 2; that of human heavy chain J region JH3 in SEQ ID NO: 3; that of human heavy chain J region JH4 in SEQ ID NO: 4; that of human heavy chain J region JH5 in SEQ ID NO: 5; and that of human heavy chain J region JH6 in SEQ ID NO: 6. The nucleotide sequence of the consensus sequence for the human heavy chain J regions is set forth in SEQ ID NO: 7. The nucleotide sequence of mouse heavy chain J region JH1 is set forth in SEQ ID NO: 8; that of mouse heavy chain J region JH2 in SEQ ID NO: 9; that of mouse heavy chain J region JH3 in SEQ ID NO: 10; and that of mouse heavy chain J region JH4 in SEQ ID NO: 11. The nucleotide sequence of the consensus sequence for the mouse heavy chain J regions is set forth in SEQ ID NO: 12. The nucleotide sequence of the human kappa J region JK1 is set forth in SEQ ID NO: 13, that of human kappa J region JK2 in SEQ ID NO: 14; that of human kapga J region JK3 in SEQ ID NO: 15; that of human kappa J region JK4 in SEQ ID NO: 16; and that of human kalga J region JK5 in SEQ ID NO: 17. The nucleotide sequence of the consensus sequence for the human kappa J regions is set forth in SEQ ID NO: 18. The nucleotide sequence of the mouse kappa J region JK1 is set forth in SEQ ID NO: 19, that of mouse kala J region JK2 in SEQ ID NO: 20; that of mouse kappa J region JK3 in SEQ ID NO: 21; that of mouse kappa J region JK4 in SEQ ID NO: 22; and that of mouse kala J region JK5 in SEQ ID NO: 23. The nucleotide sequence of the consensus sequence for the mouse kappa J regions is set forth in SEQ ID NO: 24. The oligonucleotide sequence below the mouse kappa J region consensus sequence is a Universal Immunogclobulin Gene (UIG) oligonucleotide SEQ ID NO:25 . The nucleotide sequence of the human lambda pseudo J region JPSL Iis set forth in SEQ ID NO: 26. The nucleotide sequence of the mouse lambda J region JL1 is set forth in SEQ ID NO: 27; that of mouse lambda J region JL2 in SEQ ID NO: 28; and that of mouse lambda J region JL3 in SEQ ID NO: 29. The nucleotide sequence of the consensus sequence for the mouse lambda J regions is set forth in SEQ ID NO: 30. Note that there are only a few J regions with relatively conserved sequences, especially near the constant regions, in each immunoglobulin gene locus.

FIG. 3 shows the nucleotide sequences of the mouse J regions. Shown below are the oligonucleotide primers UIG-H FIG. 3A, SEQ ID NO:35 and UIG-K. FIG. 3B SEQ ID NO:40 Note that each contains a restriction enzyme site. They can be used as primers for the synthesis of cDNA complementary to the variable region of mRNA, and can also be used to mutagenize, in vitro, cloned cDNA. The nucleotide sequence of the mouse heavy chain J segment JH1 is set forth in SEQ ID NO: 31; that of mouse heavy chain J segment JH2 in SEQ ID NO: 32; that of mouse heavy chain J segment JH3 in SEQ ID NO: 33; and that of mouse heavy chain J segment JH4 in SEQ ID NO: 34. The nucleotide sequence of the mouse kappa light chain J segment JK1 is set forth in SEQ ID NO: 36; that of mouse kappa light chain J segment JK2 in SEQ ID NO: 37; that of mouse kappa light chain J segment JK4 in SEQ ID NO: 38; and that of mouse kappa light chain J segment JK5 in SEQ ID NO: 39.

FIG. 4 Human Constant Domain Module. The human C gamma 1 clone, pGMH6, FIG. 4A was isolated from the cell line GM2146. The sequence at its $J_H$-$C_H$1 junction is shown SEQ ID NO:41. Two restriction enzyme sites are useful as joints in recombining the $C_H$1 gene with different $V_H$ genes. The ApaI site is 16 nucleotide residues into the $C_H$1 coding domain of Human gamma 1; and is used in a previous construction of a mouse-human chimeric heavy-chain immunoglobulin. The BstEII site is in the $J_H$ region, and is used in the construction described in this application.

The human $C_K$ clone, pGML60, FIG. 4B is a composite of two cDNA clones, one isolated from GM1500 (pK2–3), the other from GM2146 (pGML1). The $J_K$-$C_K$ junction sequence shown SEQ ID NO:42 comes from pk2–3. In vitro mutagenesis using the oligonucleotide, $J_K$HindIII, was carried out to engineer a HindIII site 14 nucleotide residues 5' of the J-C junction. This changes a human GTG codon into a CTT codon.

FIG. 5 shows the nucleotide sequence of the V region of the 2H7 $V_H$ cDNA clone pH2–11 (SEQ ID NO: 43, a corresponding amino acid sequence is set forth in SEQ ID NO: 44). The sequence was determined by the dideoxytermination method using M13 subclones of gene fragments. Open circles denote amino acid residues confirmed by peptide sequence. A sequence homologous to $D_{SP.2}$ in the CDR3 region is underlined. The NcoI site at 5' end was converted to a SalI site by using SalI linkers.

FIG. 6 shows the nucleotide sequeence of the V region of the 2H7 $V_K$ cDNA clone pL2–12 (SEQ ID NO: 45, a corresponding amino acid sequence is set forth in SEQ ID NO: 46). The oligonucleotide primer used for site-directed mutagenesis is shown below the $J_K$5 segment. Open circles denote amino acid residues confirmed by peptide sequence.

Figure 7A:
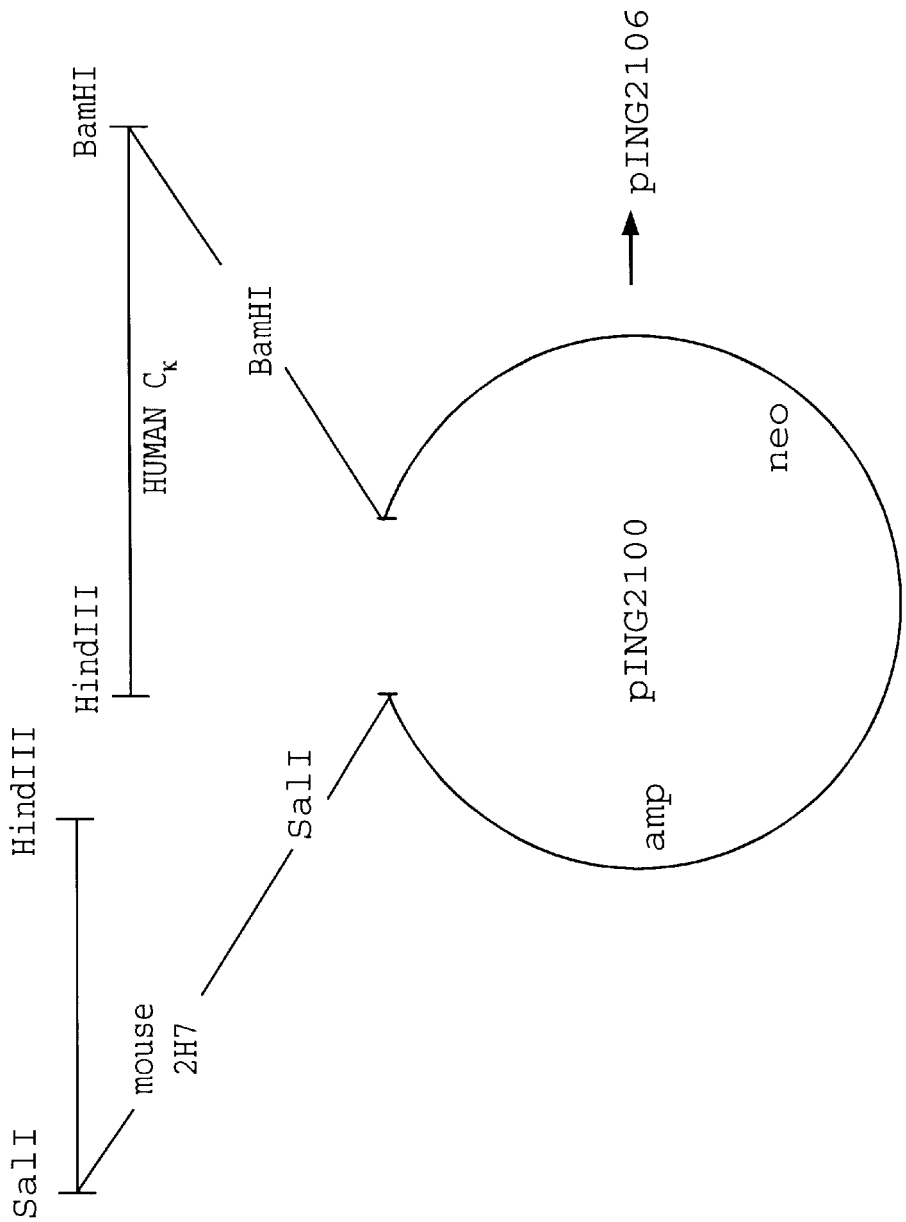
Figure 7B:
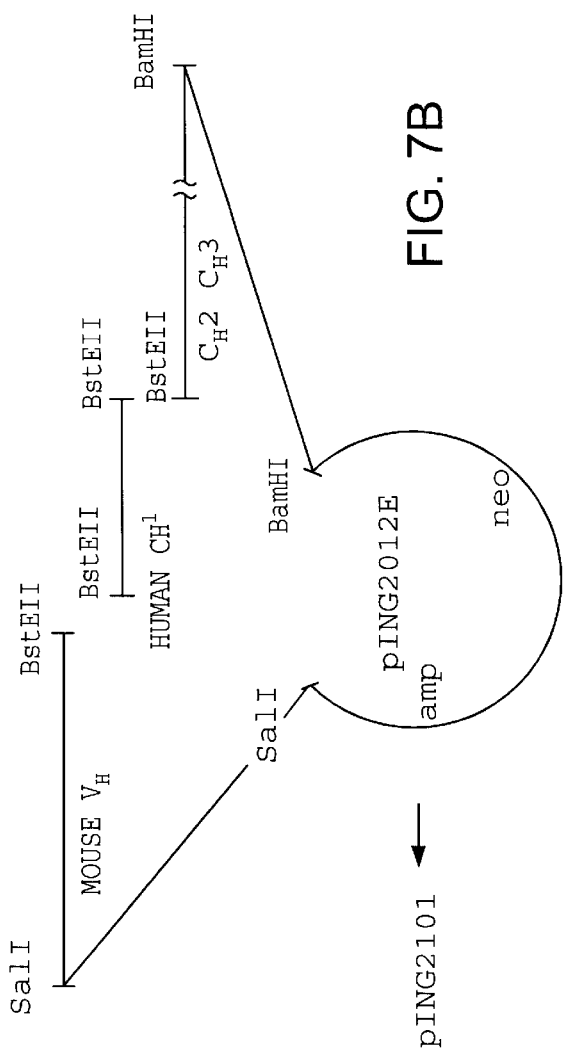
Figure 7C:
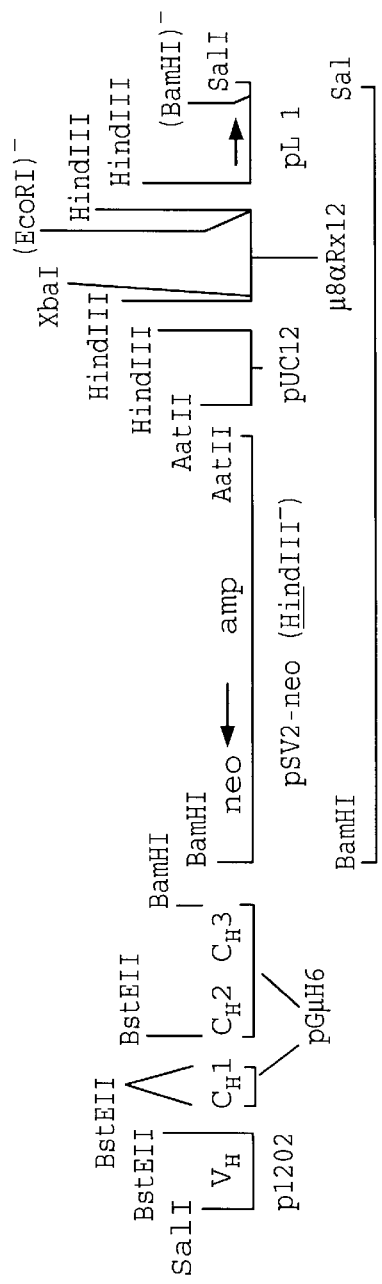

FIG. 7 shows the construction of the light and heavy chain expression plasmids pING2106 (FIG. 7A) and pING2101 (FIG. 7B). The SalI to BamHI fragment from pING2100 is identical to the SalI to BamHI fragment from pING2012E (see FIG. 7C). A linear representation of the circular plasmid pING2012E is shown in panel C. The 6.6 Kb SalI to BamHI fragment contains sequences from pSV2-neo, puc12, M8alphaRX12, and pL1. The HindIII site in pSV2-neo was destroyed before assembly of pING2012E by HindIII cleavage, fill-in, and religation.

Figure 8:
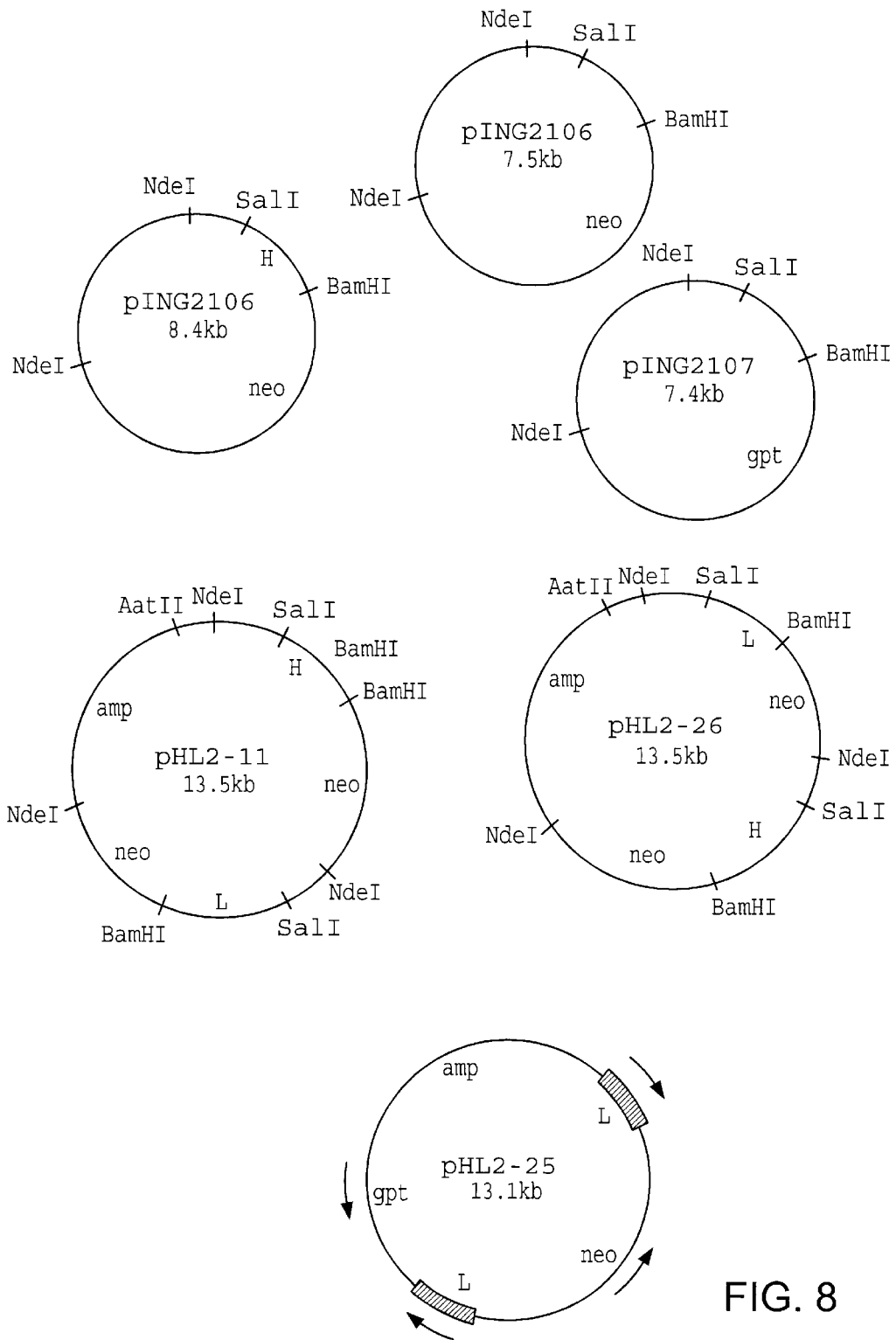

FIG. 8 shows the structure of several chimeric 2H7-$V_H$ expression plasmids. pING2107 is a gpt version of the light chain plasmid, pING2106. The larger ones are two-gene plasmids. pHL2–11 and pHL2–26 contain both H and L genes, while pLL2–25 contains two L genes. They were constructed by joining an NdeI fragment containing either an H or L gene to partially digested (with NdeI) pING2106.

Figure 9:
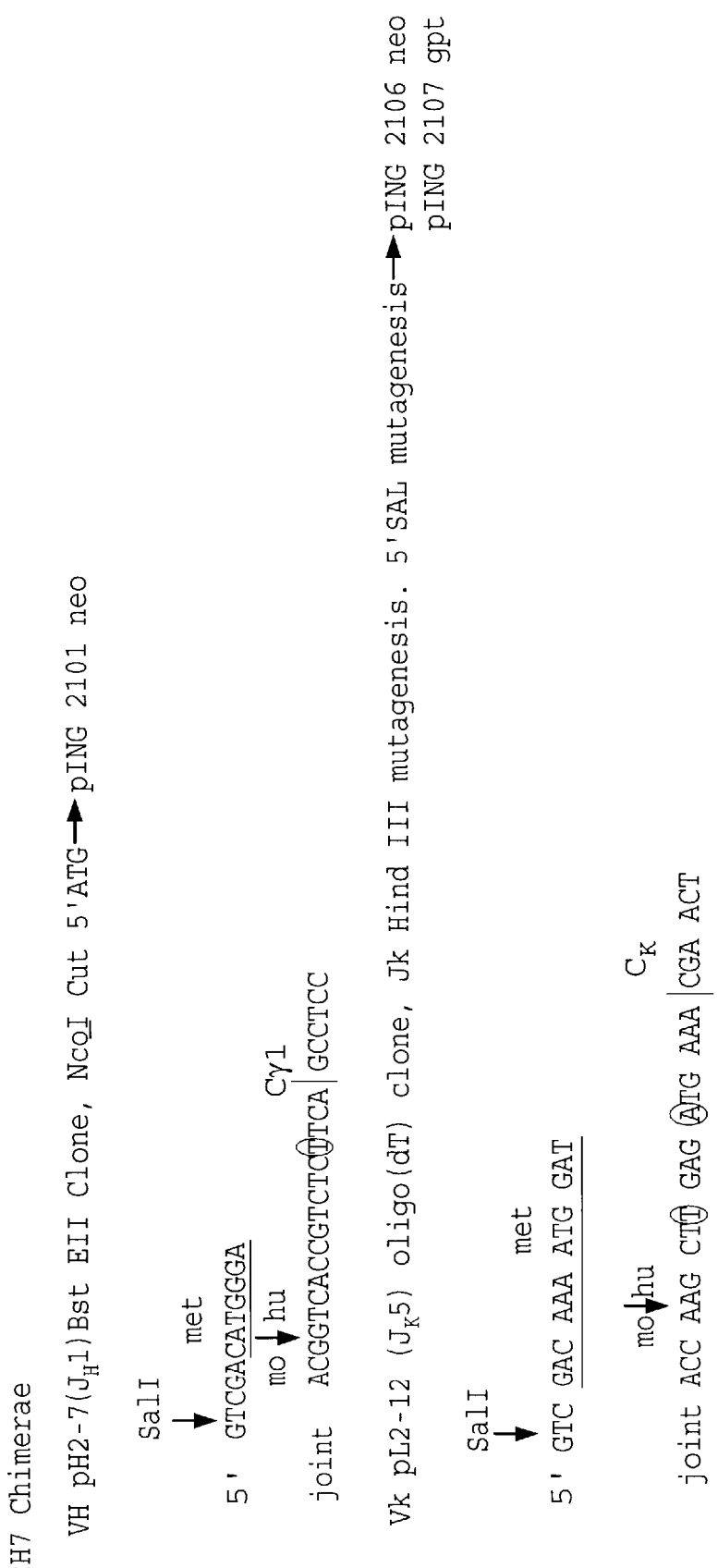

FIG. 9 shows a summary of the sequence alterations made in the construction of the 2H7 chimeric antibody expression plasmids. Residues underlined in the 5' untranslated region SEQ ID NOS:47 and 49 are derived from the cloned mouse kappa and heavy-chain genes. Residues circled in the V/C boundary SEQ ID NOS:48 and 50 result from mutagenesis operations to engineer restriction enzyme sites in this region.

DESCRIPTION OF THE PREFERRED EMBODIMENTS INTRODUCTION

Generally, antibodies are composed of two light and two heavy chain molecules. Light and heavy chains are divided into domains of structural and functional homology. The variable domains of both the light ($V_L$) and the heavy ($V_H$) chains determine recognition and specificity. The constant region domains of light ($C_L$) and heavy ($C_H$) chains confer important biological properties such as antibody chain association, secretion, transplacental mobility, complement binding, and the like.

A complex series of events leads to immunoglobulin gene expression in the antibody producing cells. The V region gene sequences conferring antigen specificity and binding are located in separate germ line gene segments called $V_H$, D and $J_H$; or $V_L$ and $J_L$. These genejsegments are joined by DNA rearrangements to form the complete V regions expressed in heavy and light chains respectively (FIG. 1). The rearranged, joined ($V_L$-$J_L$ and $V_H$-D-$J_H$) V segments then encode the complete variable regions or antigen binding domains of light and heavy chains, respectively.

Definitions

Certain terms and phrases are used throughout the specification and claims. The following definitions are provided for purposes of clarity and consistency.

1. Expression vector—a plasmid DNA containing necessary regulatory signals for the synthesis of mRNA derived from any gene sequence, inserted into the vector.

2. Module vector—a plasmid DNA containing a constant or variable region gene module.

3. Expression plasmid—an expression vector that contains an inserted gene, such as a chimeric immunoglobulin gene.

4. Gene cloning—synthesis of a gene, insertion into DNA vectors, identification by hybridization, sequence analysis and the like.

5. Transfection—the transfer of DNA into mammalian cells.

Genetic Processes and Products

The invention provides a novel approach for the cloning and production of a human/mouse chimeric antibody with specificity to a human B cell surface antigen. The antigen is a polypeptide or comprises a polypeptide bound by the 2H7 monoclonal antibody described in Clark et al. *Proc. Natl. Acad. Sci., U.S.A.* 82:1766–1770 (1985). This antigen is a phosphoprotein designated (Bp35(CD20)) and is only expressed on cells of the B cell lineage. Murine monoclonal antibodies to this antigen have been made before and are described in Clark et al., supra; see also Stashenko, P., et al., *J. Immunol.* 125:1678–1685 (1980).

The method of production combines five elements:

(1) Isolation of messenger RNA (mRNA) from the mouse hybridoma line producing the monoclonal antibody, cloning and cDNA production therefrom;

(2) Preparation of Universal Immunoglobulin Gene (UIG) oligonucleotides, useful as primers and/or probes for cloning of the variable region gene segments in the light and heavy chain mRNA from the hybridoma cell line, and cDNA production therefrom;

(3) Preparation of constant region gene segment modules by cDNA preparation and cloning, or genomic gene preparation and cloning;

(4) Construction of complete heavy or light chain coding sequences by linkage of the cloned specific immunoglobulin variable region gene segments of part (2) above to cloned human constant region gene segment modules;

(5) Expression and production of light and heavy chains in selected hosts, including prokaryotic and eukaryotic cells, either in separate fermentations followed by assembly of antibody molecules in vitro, or through production of both chains in the same cell.

One common feature of all immunoglobulin light and heavy chain genes and the encoded messenger RNAs is the so-called J region (i.e. joining region, see FIG. 1). Heavy and light chain J regions have different sequences, but a high degree of sequence homology exists (greater than 80%) especially near the constant region, within the heavy $J_H$ regions or the kappa light chain J regions. This homology is exploited in this invention and consensus sequences of light and heavy chain J regions were used to design oligonucleotides (designated herein as UIGs) for use a as primers or probes for cloning immunoglobulin light or heavy chain mRNAs or genes (FIG. 3). Depending on the sequence of a particular UIG, it may be capable of hybridizing to all immunoglobulin mRNAs or a specific one containing a particular J sequence. Another utility of a particular UIG probe may be hybridization to light chain or heavy chain mRNAs of a specific constant region, such as UIG-MJK which detects all mouse $J_K$-containing sequences (FIG. 2).

UIG design can also include a sequence to introduce a restriction enzyme site into the cDNA copy of an immunoglobulin gene (see FIG. 3). The invention may, for example, utilize chemical gene synthesis to generate the UIG probes for the cloning and modification of V regions from immunoglobulin mRNA. On the other hand, oligonucleotides can be synthesized to recognize individually, the less conserved 5'-region of the J regions as a diagnostic aid in identifying the particular J region present in the immunoglobulin mRNA.

A multi-step procedure is utilized for generating complete V+C region cDNA clones from the hybridoma cell light and heavy chain mRNAs. First, the complementary strand of oligodT-primed cDNA is synthesized, and this double-stranded cDNA is cloned in appropriate cDNA cloning vectors such as pBR322 (Gubler and Hoffman, *Gene*, 25: 263 (1983)). Clones are screened by hybridization with UIG oligonucleotide probes. Positive heavy and light chain clones identified by this screening procedure are mapped and sequenced to select those containing V region and leader coding sequences. In vitro mutagenesis including, for example, the use of UIG oligonucleotides, is then used to engineer desired restriction enzyme cleavage sites. We used this approach for the chimeric 2H7 light chain.

An expedient method is to use synthetic UIG oligonucleotides as primers for the synthesis of cDNA. This method has the advantage of simultaneously introducing a desired restriction enzyme site, such as BstEII (FIG. 3) into a V region cDNA clone. We used this approach for the chimeric 2H7 heavy chain. Second, cDNA constant region module vectors are prepared from human cells. These cDNA clones are modified, when necessary, by site-directed mutagenesis to place a restriction site at the analogous position in the human sequence or at another desired location near a boundary of the constant region. An alternative method utilizes genomic C region clones as the source for C region module vectors.

Third, cloned V region segments generated as above are excised and ligated to light or heavy chain C region module vectors. For example, one can clone the complete human kappa light chain C region and the complete human $gamma_1$ C region. In addition, one can modify the human $gamma_1$ region to introduce a termination codon and thereby obtain a gene sequence which encodes the heavy chain portion of an $F_{ab}$ molecule.

The coding sequences having operationally linked V and C regions are then transferred into appropriate expression vehicles for expression in appropriate hosts, prokaryotic or eukaryotic. Operationally linked means in-frame joining of coding sequences to derive a continuously translatable gene sequence without alterations or interruptions of the triplet reading frame.

One particular advantage of using cDNA genetic sequences in the present invention is the fact that they code continuously for immunoglobulin chains, either heavy or light. By "continuously" is meant that the sequences do not contain introns (i.e. are not genomic sequences, but rather, since derived from mRNA by reverse transcription, are sequences of contiguous exons). This characteristic of the cDNA sequences provided by the invention allows them to be expressible in prokaryotic hosts, such as bacteria, or in lower eukaryotic hosts, such as yeast.

Another advantage of using cDNA cloning method is the ease and simplicity of obtaining variable region gene modules.

The terms "constant" and "variable" are used functionally to denote those regions of the immunoglobulin chain, either heavy or light chain, which code for properties and features possessed by the variable and constant regions in natural non-chimerici antibodies. As noted, it is not necessary for the complete coding region for variable or constant regions to be present, as long as a functionally operating region is present and available.

Expression vehicles include plasmids or other vectors. Preferred among these are vehicles carrying a functionally complete human constant heavy or light chain sequence having appropriate restriction sites engineered so that any variable heavy or light chain sequence with appropriate cohesive ends can be easily inserted thereinto. Human constant heavy or light chain sequence-containing vehicles are thus an important embodiment of the invention. These vehicles can be used as intermediates for the expression of any desired complete heavy or light chain in any appropriate host.

One preferred host is yeast. Yeast provides substantial advantages for the production of immunoglobulin light and heavy chains. Yeasts carry out posttranslational peptide modifications including glycosylation. A number of recombinant DNA strategies now exist which utilize strong promoter sequences and high copy number plasmids which can be used for overt production of the desired proteins in yeast. Yeast recognizes leader sequences on cloned mammalian gene products and secretes peptides bearing leader sequences (i.e. prepeptides) (Hitzman, et al., 11th International Conference on Yeast, Genetics and Molecular Biology, Montpelier, France, Sep. 13–17, 1982).

Yeast gene expression systems can be routinely evaluated for the level of heavy and light chain production, protein stability, and secretion. Any of a series of yeast gene expression systems incorporating promoter and termination elements from the actively expressed genes coding for glycolytic enzymes produced in large quantities when yeasts are grown in mediums rich in glucose can be utilized. Known glycolytic genes can also provide very efficient transcription control signals. For example, the promoter and terminator signals of the iso-1-cytochrome C (CYC-1) gene can be utilized.

The following approach can be taken to develop and evaluate optimal expression plasmids for the expression of cloned immunoglobulin cDNAs in yeast.

(1) The cloned immunoglobulin DNA linking V and C regions is attached to different transcription promoters and terminator DNA fragments;

(2) The chimeric genes are placed on yeast plasmids (see, for example, Broach, J.R. in Methods in Enzymology—Vol. 101:307 ed. Wu, R. et al., 1983));

(3) Additional genetic units such as a yeast leader peptide may be included on immunoglobulin DNA constructs to obtain antibody secretion.

(4) A portion of the sequence, frequently the first 6 to 20 codons of the gene sequence may be modified to represent preferred yeast codon usage.

(5) The chimeric genes are placed on plasmids used for integration into yeast chromosomes.

The following approaches can be taken to simultaneously express both light and heavy chain genes in yeast.

(1) The light and heavy chain genes are each attached to a yeast promoter and a terminator sequence and placed on the same plasmid. This plasmid can be designed for either autonomous replication in yeast or integration at specific sites in the yeast chromosome.

(2) The light and heavy chain genes are each attached to a yeast promoter and terminator sequence on separate plasmids containing different selectable markers. For example, the light chain gene can be placed on a plasmid containing the trp1 gene as a selectable marker, while the heavy chain gene can be placed on a plasmid containing ura3 as a selectable marker. The plasmids can be designed for either autonomous replication in yeast or integration at specific sites in yeast chromosomes. A yeast strain defective for both selectable markers is either simultaneously or sequentially transformed with the plasmid containing the light chain gene and with the plasmid containing the heavy chain gene.

(3) The light and heavy chain genes are each attached to a yeast promoter and terminator sequence on separate plasmids each containing different selectable markers as described in (2) above. A yeast mating type "a" strain defective in the selectable markers found on the light and heavy chain expression plasmids (trp1 and ura3 in the above example) is transformed with the plasmid containing the light chain gene by selection for one of the two selectable markers (trp1 in the above example). A yeast mating type "alpha" strain defective in the same selectable markers as the "a" strain (i.e. trp1 and ura3 as examples) is transformed with a plasmid containing the heavy chain gene by selection for the alternate selectable marker (i.e. ura3 in the above example). The "a" strain containing the light chain plasmid (phenotype: Trp$^+$ Ura$^-$ in the above example) and the strain containing the heavy chain plasmid (phenotype: Trp$^-$ Ura$^+$ in the above example) are mated and diploids are selected which are prototrophic for both of the above selectable markers (Trp$^+$ Ura$^+$ in the above example).

Among bacterial hosts which may be utilized as transformation hosts, *E. coli* K12 strain 294 (ATCC 31446) is particularly useful. Other microbial strains which may be used include *E. coli* X1776 (ATCC 31537). The aforementioned strains, as well as *E. coli* W3110 (ATCC 27325) and other enterobacteria such as *Salmonella typhimurium* or *Serratia marcescens*, and various Pseudomonas species may be used.

In general, plasmid vectors containing replicon and control sequences which are derived from species compatible with a host cell are used in connection with these hosts. The vector ordinarily carries a replication site, as well as specific genes which are capable of providing phenotypic selection in transformed cells. For example, *E. coli* is readily transformed using pBR322, a plasmid derived from an *E. coli* species (Bolivar, et al., *Gene*, 2: 95 (1977)). pBR322 contains genes for ampicillin and tetracycline resistance, and thus provides easy means for identifying transformed cells. The pBR322 plasmid or other microbial plasmids must also contain, or be modified to contain, promoters which can be used by the microbial organism for expression of its own proteins. Those promoters most commonly used in recombinant DNA construction include the beta-lactamase (penicillinase) and lactose (beta-galactosidase) promoter systems (Chang et al., i Nature, 275: 615 (1978); Itakura et al., *Science*, 198:1056 (1977)); and tryptophan promoter systems (Goeddel et al., *Nucleic Acids Research*, 8: 4057 (1980); EPO Publication No. 0036776). While these are the most commonly used, other microbial promoters have been discovered and utilized.

For example, a genetic construct for any heavy or light chimeric immunoglobulin chain can be placed under the control of the leftward promoter of bacteriophage lambda ($P_L$). This promoter is one of the strongest known promoters which can be controlled. Control is exerted by the lambda repressor, and adjacent restriction sites are known.

The expression of the immunoglobulin chain sequence can also be placed under control of other regulatory sequences which may be "homologous" to the organism in its untransformed state. For example, lactose dependent *E. coli* chromosomal DNA comprises a lactose or lac operon which mediates lactose digestion by elaborating the enzyme beta-galactosidase. The lac control elements may be obtained from bacteriophage lambda pLAC5, which is infective for *E. coli*. The lac promoter-operator system can be induced by IPTG.

Other promoter/operator systems or portions thereof can be employed as well. For example, arabinose, colicine El, galactose, alkaline phosphatase, tryptophan, xylose, tac, and the like can be used.

Other preferred hosts are mammalian cells, grown in vitro in tissue culture, or in vivo in animals. Mammalian cells provide post-translational modifications to immunoglobulin protein molecules including leader peptide removal, correct folding and assembly of heavy and light chains, proper glycosylation at correct sites, and secretion of functional antibody protein.

Mammalian cells which may be useful as hosts for the production of antibody proteins include cells of lymphoid origin, such as the hybridoma Sp2/0-Ag14 (ATCC CRL 1581) or the myeloma P3X63Ag8 (ATCC TIB 9), and its derivatives. Others include cells of fibroblast origin, such as Vero (ATCC CRL 81) or CHO-K1 (ATCC CRL 61).

Several possible vector systems are available for the expression of cloned heavy chain and light chain genes in mammalian cells. One class of vectors relies upon the integration of the desired gene sequences into the host cell genome. Cells which have stably integrated DNA can be selected by simultaneously introducing drug resistance genes such as *E. coli* gpt (Mulligan, R. C. and Berg, P., *Proc. Natl. Acad. Sci., USA*, 78: 2072 (1981)) or Tn5 neo (Southern, P. J. and Berg, P., *J. Mol. Appl. Genet.*, 1: 327 (1982)). The selectable marker gene can be either linked to the DNA gene sequences to be expressed, or introduced into the same cell by co-transfection (Wigler, M. et al., *Cell*, 16: 77 (1979)). A second class of vectors utilizes DNA elements which confer autonomously replicating capabilities to an extrachromosomal plasmid. These vectors can be derived from animal viruses, such as bovine papillomavirus (Sarver, N. et al., *Proc. Natl. Acad. Sci., USA*, 79: 7147 (1982)), polyoma virus (Deans, R. J. et al., *Proc. Natl. Acad. Sci.,*

USA, 81: 1292 (1984)), or SV40 virus (Lusky, M. and Botchan, M., *Nature*, 293: 79 (1981)).

Since an immunoglobulin cDNA is comprised only of sequences representing the mature mRNA encoding an antibody protein additional gene expression elements regulating transcription of the gene and processing of the RNA are required for the synthesis of immunoglobulin mRNA. These elements may include splice signals, transcription promoters, including inducible promoters enhancers, and termination signals. cDNA expression vectors incorporating such elements include those described by Okayama, H. and Berg, P., *Mol. Cell Biol.*, 3: 280 (1983); Cepko, C. L. et al., *Cell*, 37: 1053 (1984); and Kaufman, R. J., *Proc. Natl. Acad. Sci., USA*, 82: 689 (1985).

An additional advantage of mammalian cells as hosts is their ability to express chimeric immunoglobulin genes which are derived from genomic sequences. Thus, mammalian cells may express chimeric immunoglobulin genes which are comprised of a variable region cDNA module plus a constant region which is composed in whole or in part of genomic sequences. Several human constant region genomic clones have been described (Ellison, J. W. et al., *Nucl. Acids Res.*, 10: 4071 (1982), or Max, E. et al., *Cell*, 29: 691 (1982)). The use of such genomic sequences may be convenient or the simultaneous introduction of immunoglobulin enhancers, splice signals, and transcription termination signals along with the constant region gene segment.

Different approaches can be followed to obtain complete $H_2L_2$ antibodies.

First, one can separately express the light and heavy chains followed by in vitro assembly of purified light and heavy chains into complete $H_2L_2$ IgG antibodies. The assembly pathways used for generation of complete $H_2L_2$ IgG molecules in cells have been extensively studied (see, for example, Scharff, M., *Harvey Lectures*, 69: 125 (1974)). In vitro reaction parameters for the formation of IgG antibodies from reduced isolated light and heavy chains have been defined by Beychok, S., *Cells of Immunoglobulin Synthesis*, Academic Press, New York, page 69, 1979.

Second, it is possible to co-express light and heavy chains in the same cells to achieve intracellular association and linkage of heavy and light chains into complete $H_2L_2$ IgG antibodies. The co-expression can occur by using either the same or different plasmids in the same host.

Polypeptide Products

The invention provides "chimeric" immunoglobulin chains, either heavy or light. A chimeric chain contains a constant region substantially similar to that present in a natural human immunoglobulin, and a variable region having the desired antigenic specificity of the invention, i.e., to the specified human B cell surface antigen.

The invention also provides immunoglobulin molecules having heavy and light chains associated so that the overall molecule exhibits any desired binding and recognition properties. Various types of immunoglobulin molecules are provided: monovalent, divalent, molecules with chimeric heavy chains and non-chimeric light chains, or molecules with the invention's variable binding domains attached to moieties carrying desired functions.

Antibodies having chimeric heavy chains of the same or different variable region binding specificity and non-chimeric (i.e., all human or all non-human) light chains, can be prepared by appropriate association of the needed polypeptide chains. These chains are individually prepared by the modular assembly methods of the invention.

Uses

The antibodies of the invention having human constant region can be utilized for passive immunization, especially in humans, without negative immune reactions such as serum sickness or anaphylactic shock. The antibodies can, of course, also be utilized in prior art immunodiagnostic assays and kits in detectably labelled form (e.g., enzymes, $^{125}I$, $^{14}C$, fluorescent labels, etc.), or in immunobilized form (on polymeric tubes, beads, etc.), in labelled form for in vivo imaging, wherein the label can be a radioactive emitter, or an NMR contrasting agent such as a carbon-13 nucleus, or an X-ray contrasting agent, such as a heavy metal nucleus. The antibodies can also be used for in vitro localization of the antigen by appropriate labelling.

The antibodies can be used for therapeutic purposes, by themselves, in complement mediated lysis, or coupled to toxins or therapeutic moieties, such as ricin, etc.

Mixed antibody-enzyme molecules can be used for immunodiagnostic methods, such as ELISA. Mixed antibody-peptide effector conjugates can be used for targeted delivery of the effector moiety with a high degree of efficacy and specificity.

Specifically, the chimeric antibodies of this invention can be used for any and all uses in which the murine 2H7 monoclonal antibody can be used, with the obvious advantage that the chimeric ones are more compatible with the human body.

Having now generally described the invention, the same will be further understood by reference to certain specific examples which are included herein for purposes of illustration only and are not intended to be limiting unless otherwise specified.

Experimental

Materials and Methods

Tissue Culture Cell Lines

The human cell lines GM2146 and GM1500 were obtained from the Human Mutant Cell Repository (Camden, N.J.) and cultured in RPMI1640 plus 10% fetal bovine serum (M. A. Bioproducts). The cell line Sp2/0 was obtained from the American Type Culture Collection and grown in Dulbecco's Modified Eagle Medium (DMEM) plus 4.5 g/l glucose (M. A. Bioproducts) plus 10% fetal bovine serum (Hyclone, Sterile Systems, Logan, Utah). Media were supplemented with penicillin/streptomycin (Irvine Scientific, Irvine, Calif.

Recombinant Plasmid and Bacteriophage DNAs

The plasmids pBR322, pL1 and pUC12 were purchased from Pharmacia P-L Biochemicals (Milwaukee, Wis. The plasmids pSV2-neo and pSV2-gpt were obtained from BRL (Gaithersburg, Md.), and are available from the American Type Culture Collection (Rockville, Md.). pHu-gamma-1 is a subclone of the 8.3 Kb HindIII to BamHI fragment of the human IgG1 chromosomal gene. An isolation method for of the human IgG1 chromosomal gene is described by Ellison, J. W. et al., *Nucl. Acids Res.*, 10: 4071 (1982). M8alphaRX12 contains the 0.7 Kb XbaI to EcoRI fragment containing the mouse heavy chain enhancer from the J-C intron region of the M603 chromosomal gene (Davis, M. et al., *Nature*, 283:733, 1979) inserted into M13 mp10. DNA manipulations involving purification of plasmid DNA by buoyant density centrifugation, restriction endonuclease digestion, purification of DNA fragments by agarose gel electrophoresis, ligation and transformation of *E. coli* were as described by Maniatis, T. et al., *Molecular Cloning: A Laboratory Manual*, (1982) or other procedures. Restriction endonucleases and other DNA/RNA modifying enzymes were purchased from Boehringer-Mannheim (Indianapolis, Ind.), BRL, New England Biolabs (Beverly, Massachusetts) and Pharmacia P-L.

Oligonucleotide Preparation

Oligonucleotides were either synthesized by the triester method of Ito et al. (*Nucl. Acids Res.*, 10: 1755 (1982)), or were purchased from ELESEN, Los Angeles, Calif. Tritylated, deblocked oligonucleotides were purified on Sephadex-G50, followed by reverse-phase HPLC with a 0–25% gradient of acetonitrile in 10 mM triethylamine-acetic acid, pH 7.2, on a C18 Bondapak column (Waters Associates). Detritylation was in 80% acetic acid for 30 min., followed by evaporation thrice oligonucleotides were labeled with [gamma-$^{32}$P]ATP by T4 polynucleotide kinase.

RNA Preparation and Analysis

Total cellular RNA was prepared from tissue culture cells by the method of Auffray, C. and Rougeon, F. (*Eur. J. Biochem.*, 107: 303 (1980)) or Chirgwin, J. M. et al. (*Biochemistry*, 18: 5294 (1979)). Preparation of poly(A)$^+$ RNA, methyl-mercury agarose gel electrophoresis, and "Northern" transfer to nitrocellulose were as described by Maniatis, T. et al., supra. Total cellular RNA or poly(A)$^+$ RNA was directly bound to nitrocellulose by first treating the RNA with formaldehyde (White, B. A. and Bancroft, F. C., *J. Biol. Chem.*, 257: 8569 (1982)). Hybridization to filterbound RNA was with nick-translated DNA fragments using conditions described by Margulies, D. H. et al. (*Nature*, 295: 168 (1982)) or with $^{32}$P-labelled oligonucleotide using 4×SSC, 10×Denhardt's, 100 ug/ml salmon sperm DNA at 37° C. overnight, followed by washing in 4×SSC at 37° C.

cDNA Preparation and Cloning

Oligo-dT primed cDNA libraries were prepared from poly(A)$^+$ RNA from. GM1500 and GM2146 cells by the methods of Land, H. et al. (*Nucl. Acids Res.*, 9: 2251 (1981)) and Gubler, V. and Hoffman, B. J., *Gene*, 25: 263 (1983), respectively. The cDNA libraries were screened by hybridization (Maniatis, T., supra) with $^{32}$P-labelled oligonucleotides using the procedure of de Lange et al. (*Cell*, 34: 891 (1983)), or with nick-translated DNA fragments.

Oligonucleotide Primer Extension and Cloning

Poly(A)$^+$ RNA (20 ug) was mixed with 1.2 ug primer in 40 ul of 64 mM KCl. After denaturation at 90° C. for 5 min. and then chilling in ice, 3 units Human, Placental Ribonuclease Inhibitor (BRL) was added in 3 ul of 1M Tris-HCl, pH 8.3. The oligonucleotide was annealed to the RNA at 42° C. for 15 minutes, then 12 ul of 0.05M DTT, 0.05M MgCl$_2$, and 1 mM each of dATP, dTTP, dCTP, and dGTP was added. 2 ul of alpha-$^{32}$P-dATP (400 Ci/mmol, New England Nuclear) was added, followed by 3 ul of AMV reverse transcriptase (19 units/ul, Life Sciences).

After incubation at 42° C. for 105 min., 2 ul 0.5 M EDTA and 50 ul 10 mM Tris, 1 mM EDTA, pH 7.6 were added. Unincorporated nucleotides were removed by Sephadex G-50 spin column chromatography, and the RNA-DNA hybrid was extracted with phenol, then with chloroform, and precipitated with ethanol. Second strand synthesis, homopolymer tailing with dGTP or dCTP, and insertion into homopolymer tailed vectors was as described by Gubler and Hoffman, supra.

Site-Directed Mutagenesis

Single stranded M13 subclone DNA (1 ug) was combined with 20 ng oligonucleotide primer in 12.5 ul of Hin buffer (7 mM Tris-HCl, pH 7.6, 7 mM MgCl$_2$, 50 mM NaCl). After heating to 95° C. in a sealed tube, the primer was annealed to the template by slowly cooling from 70° C. to 37° C. for 90 minutes. 2 ul dNTPs (1 mM each), 1 ul $^{32}$P-ATP (10 uCi), 1 ul DTT (0.1 M) and 0.4 ul Klenow DNA PolI (2u, Boehringer Mannheim) were added and chains extended at 37° C. for 30 minutes. To this was added 1 ul (10 ng) M13 reverse primer (New England Biolabs), and the heating/annealing and chain extension steps were repeated. The reaction was stopped with 2 ul of 0.5M EDTA, pH 8, plus 80 ul of 10 mM Tris-HCl, pH 7.6, 1 mM EDTA. The products were phenol extracted and purified by Sephadex G-50 spun column chromatography and ethanol precipitated prior to restriction enzyme digestion and ligation to the appropriate vector.

Transfection of Myeloma Tissue Culture Cells

The electroporation method of Potter, H. et al. (*Proc. Natl. Acad. Sci., USA*, 81: 7161 (1984)) was used. After transfection, cells were allowed to recover in complete DMEM for 48–72 hours, then were seeded at 10,000 to 50,000 cells per well in 96-well culture plates in the presence of selective medium. G418 (GIBCO) selection was at 0.8 mg/ml, and mycophenolic acid (Calbiochem) was at 6 ug/ml plus 0.25 mg/ml xanthine.

Assays for Immunoglobulin Synthesis and Secretion

Secreted immunoglobulin was measured directly from tissue culture cell supernatants. Cytoplasmic protein extract was prepared by vortexing 10$^6$ cells in 160 ul of 1% NP40, 0.15 M NaCl, 10 mM Tris, 1 mM EDTA, pH 7.6 and leaving the lysate at 0° C., 15 minutes, followed by centrifugation at 10,000×g to remove insoluble debris.

A double antibody sandwich ELISA (Voller, A. et al., in *Manual of Clinical Immunology*, 2nd Ed., Eds. Rose, N. and Friedman, H., pp. 359–371, 1980) using affinity purified antisera was used to detect specific immunoglobulins. For detection of human IgG, the plate-bound antiserum is goat anti-human IgG (KPL, Gaithersburg, Maryland) at 1/1000 dilution, while the aperoxidase-bound antiserum is goat anti-human IgG (KPL or Tago, Burlingame) at 1/4000 dilution. For detection of human immunoglobulin kappa, the plate-bound antiserum is goat anti-human kappa (Tago) at 1/500 dilution, while the peroxidase-bound antiserum is goat anti-human kappa (Cappel) at 1/1000 dilution.

EXAMPLE 1

A Chimeric Mouse-Human Immunoglobulin With Specificity for a Human B-Cell. Surface Antigen (1) Antibody 2H7.

The 2H7 mouse monoclonal antibody (gamma 2b, kappa) recognizes a human B-cell surface antigen, (Bp35(CD20)) Clark, E.A., et al., *Proc. Natl. Acad. Sci., U.S.A.* 82:1766 (1985)). The (Bp35(CD20)) molecules presumably play a role in B-cell activation. The antibody 2H7 does not react with stem cells which are progenitors of B-cells epithelial, mesenchymal and fibroblastic cells of other organs.

(2) Identification of J Sequences in the Immunoglobulin mRNA of 2H7.

Frozen cells were thawed on ice for 10 minutes and then at room temperature. The suspension was diluted with 15 ml PBS and the cells were centrifuged down. They were resuspended, after washes in PBS, in 16 ml 3M LiCl, 6M urea and disrupted in a polytron shear. The preparation of mRNA and the selection of the poly(A+) fraction were carried out according to Auffray, C. and Rougeon, F., *Eur. J. Biochem.* 107:303, 1980.

The poly (A+) RNA from 2H7 was hybridized individually with labeled $J_H1$, $J_H2$, $J_H3$ and $J_H4$ oligonucleotides under conditions described by Nobrega et al. *Anal. Biochem* 131:141, 1983). The products were then subjected to electrophoresis in a 1.7% agarose-TBE gel. The gel was fixed in 10% TCA, blotted dry and exposed for autoradiography. The result showed that the 2H7 $V_H$ contains $J_H1$, $J_H2$, or $J_H4$ but not $J_H3$ sequences.

For the analysis of the $V_K$ mRNA, the dot-blot method of White and Bancroft *J. Biol. Chem.* 257:8569, (1982) was used. Poly (A+) RNA was immobilized on nitrocellulose filters and was hybridized to labeled probe-oligonucleotides at 40° in 4×SSC. These experiments show that 2H7 contains $J_K5$ sequences.

(3) V Region cDNA Clones.

A library primed by oligo (dT) on 2H7 poly (A+) RNA was screened for kappa clones with a mouse $C_K$ region probe. From the 2H7 library, several clones were isolated. A second screen with a 5' $j_K5$ specific probe identified the 2H7 ($J_K5$) light-chain clones. Heavy chain clones of 2H7 were generated by priming the poly(A+) RNA with the UIGH (BstEII) oligonucleotide (see FIG. 3), and identified by screening with the UIGH(BstEII) oligonucleotide.

The heavy and light chain genes or gene fragments from the $V_H$ and $V_K$ cDNA clones pH2-11 and pL2-12 were inserted into M13 bacteriophage vectors for nucleotide sequence analysis. The complete nucleotide sequences of the variable region of these clones were determined (FIGS. 5 and 6) by the dideoxy chain termination method. These sequences predict V region amino acid compositions that agree well with the observed compositions, and predict peptide sequences which have been verified by direct amino acid sequencing of portions of the V regions.

The nucleotide sequences of the cDNA clones show that they are immunoglobulin V region clones as they contain amino acid residues diagnostic of V domains (Kabat et al., *Sequences of Proteins of Immunological Interest;* U.S. Dept of HHS, 1983).

The 2H7 $V_H$ has the $J_H1$ sequence. The 2H7 $V_L$ is from the $V_K$-KpnI family (Nishi et al. *Proc. Nat. Acd. Sci. USA* 82:6399, 1985), and uses $J_K5$. The cloned 2H7 $V_L$ predicts an amino acid sequence which was confirmed by amino acid sequencing of peptides from the 2H7 light chain corresponding to residues 81–100. The cloned 2H7 $V_H$ predicts an amino acid sequence confirmed also by peptide sequencing, namely residues 1–12.

(4) In Vitro Mutagenesis to Engineer Restriction Enzyme Sites in the J Region for Joining to a Human C-Module, and to Remove Oligo (dC) Sequences 5' to the V Modules.

For the 2H7 $V_K$, the J-region mutagenesis primer $J_K$HindIII, as shown in FIG. 6, was utilized. A human $C_K$ module derived from a cDNA clone was also mutagenized to contain the HindIII sequence (see FIG. 4). The mutagenesis reaction was performed on M13 subclones of these genes. The frequency of mutant clones ranged from 0.5 to 1% of the plaques obtained.

It had been previously observed that the oligo (dC) sequence upstream of the AUG codon in a $V_H$ chimeric gene interferes with proper splicing in one particular gene construct. It was estimated that perhaps as much as 70% of the RNA transcripts had undergone the mis-splicing, wherein a cryptic 3' splice acceptor in the leader sequence was used. Therefore the oligo (dC) sequence upstream of the initiator AUG was removed in all of the clones.

In one approach, an oligonucleotide was used which contains a SalI restriction site to mutagenize the 2H7 $V_K$ clone. The primer used for this oligonucleotidedirected mutagenesis is a 22-mer which introduces a SalI site between the oligo (dC) and the initiator met codon (FIG. 6).

In a different approach, a convenient NcoI site was utilized to delete the 5' untranslated region and oligo (dC) of the 2H7 $V_H$ clone (see FIG. 5).

The human C gamma 1 gene module is a cDNA derived from GM2146 cells (Human Genetic Mutant Cell Repository, Newark, N.J.). This C gamma 1 gene module was previously combined with a mouse $V_H$ gene module to form the chimeric expression plasmid pING2012E (FIG. 7C).

(5) Chimeric 2H7 Expression Plasmids.

A 2H7 chimeric heavy chain expression plasmid was derived from the replacement of the $V_H$ module of pING2012E with the $V_H$ cDNA modules to give the expression plasmid pING2101 (FIG. 7b). This plasmid directs the synthesis of chimeric 2H7 heavy chain when transfected into mammalian cells.

For the 2H7 light chain chimeric gene, the SalI to HindIII fragment of the mouse $V_K$ module was joined to the human $C_K$ module by the procedure outlined in FIG. 7a, forming pING2106. Replacement of the neo sequence with the *E. coli* gpt gene derived from pSV2-gpt resulted in pING2107, which expresses 2H7 chimeric light chain and confers mycophenolic acid resistance when transfected into mammalian cells.

The inclusion of both heavy and light chain chimeric genes in the same plasmid allows for the introduction into transfected cells of a 1:1 gene ratio of heavy and light chain genes leading to a balanced-gene dosage. This may improve expression and decrease manipulations of transfected cells for optimal chimeric antibody expression. For this purpose, the DNA fragments derived from the chimeric heavy and light chain genes of pING2101 and pING2106 were combined into the expression plasmids pHL2-11 and pHL2-26 (FIG. 8). This expression plasmid contains a selectable neor marker and separate transcription units for each chimeric gene, each including a mouse heavy chain enhancer.

The modifications and V-C joint regions of the 2H7 chimeric genes are summarized in FIG. 9.

(6) Stable Transfection of Mouse Lymphoid Cells for the Production of Chimeric Antibody.

Electroporation was used (Potter et al supra; Toneguzzo et al. *Mol. Cell Biol.* 6:703 1986) for the introduction of 2H7 chimeric expression plasmid DNA into mouse Sp2/0 cells. The electroporation technique gave a transfection frequency of $10^{-4} \times 10^{-5}$ for the Sp2/0 cells.

The expression plasmids, pING2101 and pING2106, were digested with NdeI; and the DNA was introduced into Sp2/0 cells by electroporation. Transformant 1D6 was obtained which secretes chimeric 2H7 antibody. Antibody isolated from this cell line was used for the functional assays done to characterize the chimeric antibody. We have also obtained transformants from experiments using the two-gene plasmids.

(7) Purification of Chimeric 2H7 Antibody Secreted in Tissue Culture.

a. 1D6 (Sp2/0. pING2101/pING2106.1D6) cells were grown in culture medium [DMEM (Gibco #320–1965), supplemented with 10% Fetal Bovine Serum (Hyclone #A-1111-D), 10 mM HEPES, 1× Glutamine-Pen-Strep (Irvine Scientific #9316) to $1 \times 10^6$ cell/ml.

b. The cells were then centrifuged at 400×g and resuspended in serum-free culture medium at $2 \times 10^6$ cell/ml for 18–24 hr.

c. The medium was centrifuged at 4000 RPM in a JS-4.2 rotor (3000×g) for 15 min.

d. 1.6 liter of supernatant was then filtered through a 0.45 micron filter and then concentrated over a YM30 (Amicon Corp.) filter to 25 ml.

e. The conductance of the concentrated supernatant was adjusted to 5.7–5.6 mS/cm CDM 80 radiometer and the pH was adjusted to 8.0.

f. The supernatant was centrifuged at 2000×g, 5 min., and then loaded onto a 40 ml DEAE column, which was pre-equilibrated with 10 mM sodium phosphate, pH8.0.

g. The flow through fraction was collected and loaded onto a 1 ml protein A-Sepharose (Sigma) column preequilibrated with 10 mM sodium phosphate, pH8.0.

h. The column was washed first with 6 ml 10 mM sodium phosphate buffer pH 8.0, followed by 8 ml 0.1M sodium citrate pH 3.5, then by 6 ml 0.1M citric acid (pH 2.2). Fractions of 0.5 ml were collected in tubes containing 50 ul 2M Tris base (Sigma).

i. The bulk of the IgG was in the pH 3.5 elution and was pooled and concentrated over Centricon 30 (Amicon Corp.) to approximately 0.06 ml.

The buffer was changed to PBS (10 mM sodium phosphate pH 7.4, 0.15M NaCl) in Centricon 30 by repeated diluting with PBS and reconcentrating.

k. The IgG solution was then adjusted to 0.10 ml and bovine serum albumin (Fraction V, U.S. Biochemicals) was added to 1.0% as a stabilizing reagent.

(9) Chimeric 2H7 Antibody, Like the Mouse 2H7 Antibody, Specifically Binds to Human B Cells.

First, the samples were tested with a binding assay, in which cells of both an 2H7 antigen-positive and an 2H7 antigen-negative cell line were incubated with standard mouse monoclonal antibody 2H7 with chimeric 2H7 antibody derived from the cell culture supernatants, followed by a second reagent, fluorescein-isothiocyanate (FITC)-conjugated goat antibodies to human (or mouse, for the standard) immunoglobulin.

Binding Assays. Cells from a human B cell line, T51, were used. Cells from human colon carcinoma line C3347 were used as a negative control, since they, according to previous testing, do not express detectable amounts of the 2H7 antigen. The target cells were first incubated for 30 min at 4° C. with either the chimeric 2H7 or with mouse 2H7 standard, which had been purified from mouse ascites. This was followed by incubation with a second, FITC-labelled, reagent, which for the chimeric antibody was goat-anti-human immunoglobulin, obtained from TAGO (Burlingame, Calif.), and used at a dilution of 1:50. For the mouse standard, it was goat-anti-mouse immunoglobulin, also obtained from TAGO and used at a dilution of 1:50. Antibody binding to the cell surface was determined using a Coulter Model EPIC-C cell sorter.

As shown in Table I, both the chimeric and the mouse standard 2H7 bound significantly, and to approximately the same extent, to the positive T51 line. They did not bind above background to the 2H7 negative C-3347 line.

Functional Assays.

In previous studies, antibody 2H7 was tested for antibody-dependent cellular cytotoxicity (ADCC) measured by its ability to lyse $^{51}$Cr-labelled human B lymphona cells in the presence of human peripheral blood leukocytes as the source of effector cells. It was also tested for its ability to lyse $^{51}$Cr labelled hum B cells in the presence of human serum as the source of complement. These tests were carried out as previously described for mouse monoclonal anti-carcinoma antibody L6, which can mediate ADCC, as well as complement-mediated cytoxicity, CDC. The techniques used and the data described for the L6 antibody have been previously described. Hellstrom, et al., *Proc. Natl. Acad Sci. U.S.A.* 83: 7059–7063 (1986).

Chimeric 2H7, but not mouse 2H7 antibody, can mediate both ADCC and CDC against human B lymphoma cells. Thus a hybridoma producing a non-functional mouse antibody can be converted to a hybridoma producing a chimeric antibody with ADCC and CDC activities. Such a chimeric antibody is a prime candidate for the treatment or imaging of B-cell disorders, such as leukemias, lymphomas, and the like.

This invention therefore provides a method for making biologically functional antibodies when starting with a hybridoma which produces antibody which has the desired specificity for antigen but lacks biological effector functions such as ADCC and CDC.

Conclusions.

The results presented above demonstrate that the chimeric 2H7 antibody binds to (Bp35(CD20)) antigen positive human B cells to approximately the same extent as the mouse 2H7 monoclonal antibody. This is significant because the 2H7 antibody defines a surface phosphoprotein antigen (Bp35(CD20)), of about 35,000 daltons, which is expressed on the cells of B cell lineage. The 2H7 antibody does not bind detectably to various other cells such as fibroblasts, endothelial cells, or epithelial cells in the major organs or the stem cell precursors which give rise to B cells.

Although the prospect of attempting tumor therapy using monoclonal antibodies is attractive, with some partial tumor regressions being reported, to date such monoclonal antibody therapy has been met with limited success (Houghton et al., February 1985, *Proc. Natl. Acad. Sci.* 82:1242–1246). Murine monoclonal anti-(Bp35(CD20)) antibody has been used for therapy of B cell malignancies (Press, et al.,) Blood: Feb. 1987, in press). The therapeutic efficacy of mouse monoclonal antibodies (which are the ones that have been tried so far) appears to be too low for most practical purposes. Because of the "human" properties St which may make the chimeric 2H7 monoclonal antibodies more resistant to clearance and less immunogenic in vivo, the chimeric 2H7 monoclonal antibodies will be advantageously used not only for therapy with unmodified chimeric antibodies, but also for development of various immunoconjugates with drugs, toxins, immunomodulators, isotopes, etc., as well as for diagnostic purposes such as in vivo imaging of B-cell tumors (for example, lymphomas and leukemias) using appropriately labelled chimeric 2H7 antibodies. Such immunoconjugation techniques are known to those skilled in the art and can be used to modify the chimeric 2H7 antibody molecules of the present invention. The chimeric 2H7 antibody, by virtue of its having the human constant portion, will possess biological activity in complement dependent and antibody dependent cytotoxicity which the mouse 2H7 does not.

An illustrative cell line secreting chimeric 2H7 antibody was deposited prior to the U.S. filing date at the ATCC, 1080 Universite Boulevard, Manassas, Va. 20110. This is a transfected hybridoma (corresponds to 1D6 cells supra) ATCC HB 9303.

The present invention is not to be limited in scope by the cell lines deposited since the deposited embodiment is intended as a single illustration of one aspect of the invention and all cell lines which are functionally equivalent are within the scope of the invention. Indeed, various modifications of the invention in addition to those shown in the art from the foregoing description and accompanying drawings. Such modifications are intended to fall within the scope of the appended claims.

TABLE 1

Binding Assays Of Chimeric 2H7 Antibody and Mouse 2H7 Monoclonal Antibody to a B cell Line Expressing (Bp35(CD20)) and a Cell Line Not Expressing This Antigen.

| Antibody | GAM | GAH |
|---|---|---|
| | Binding Ratio* for T51 B-Cells | |
| 2H7 Mouse | 37 | ND |
| 2H7 Chimeric | ND | 29 |
| L6 Mouse | 1 | ND |
| | Binding Ratio* for C3347 Cells | |
| 2H7 Mouse | 1.4 | ND |
| 2H7 Chimeric | ND | 1.3 |
| L6 Mouse | 110 | ND |

*All assays were conducted using an antibody concentration of 10 ug/ml. The binding ratio is the number of times brighter a test sample is than a control sample treated with GAM (FITC-Conjugated goat anti-mouse) or GAH (FITC conjugated goat anti-human) alone.
A ratio of 1 means that the test sample is just as bright as the control;
a ratio of 2 means the test sample is twice as bright as the control and so on.
ND—not done

SEQUENCE LISTING

<160> NUMBER OF SEQ ID NOS: 50

<210> SEQ ID NO 1
<211> LENGTH: 52
<212> TYPE: DNA
<213> ORGANISM: Homo sapiens

<400> SEQUENCE: 1
gctgaatact tccagcactg gggccagggc accctggtca ccgtctcctc ag          52

<210> SEQ ID NO 2
<211> LENGTH: 53
<212> TYPE: DNA
<213> ORGANISM: Homo sapiens

<400> SEQUENCE: 2
ctactggtac ttcgatctct ggggccgtgg caccctggtc actgtctcct cag         53

<210> SEQ ID NO 3
<211> LENGTH: 48
<212> TYPE: DNA
<213> ORGANISM: Homo sapiens

<400> SEQUENCE: 3
atgcttttga tgtctggggc caagggacaa tggtcaccgt ctcttcag               48

<210> SEQ ID NO 4
<211> LENGTH: 48
<212> TYPE: DNA
<213> ORGANISM: Homo sapiens

<400> SEQUENCE: 4
actactttga ctactggggc caaggaaccc tggtcaccgt ctcctcag               48

<210> SEQ ID NO 5
<211> LENGTH: 50
<212> TYPE: DNA
<213> ORGANISM: Homo sapiens

<400> SEQUENCE: 5
acactggttc gactcctggg gccaaggaac cctggtcacc gtctcctcag             50

<210> SEQ ID NO 6
<211> LENGTH: 63
<212> TYPE: DNA
<213> ORGANISM: Homo sapiens

<400> SEQUENCE: 6
attactacta ctactacggt atggacgtct gggggcaagg gaccacggtc accgtctcct  60
cag                                                               63

<210> SEQ ID NO 7
<211> LENGTH: 42
<212> TYPE: DNA
<213> ORGANISM: Artificial sequence
<220> FEATURE:
<223> OTHER INFORMATION: Consensus of human heavy chain J regions

<400> SEQUENCE: 7
tcgacctctg gggccaagga accctggtca ccgtctcctc ag                    42

```
<210> SEQ ID NO 8
<211> LENGTH: 52
<212> TYPE: DNA
<213> ORGANISM: mus musculus

<400> SEQUENCE: 8
tactggtact tcgatgtctg gggcgcaggg accacggtca ccgtctcctc ag        52

<210> SEQ ID NO 9
<211> LENGTH: 46
<212> TYPE: DNA
<213> ORGANISM: mus musculus

<400> SEQUENCE: 9
tactttgact actggggcca aggcaccact ctcacagtct cctcag              46

<210> SEQ ID NO 10
<211> LENGTH: 48
<212> TYPE: DNA
<213> ORGANISM: mus musculus

<400> SEQUENCE: 10
cctggtttgc ttactggggc caagggactc tggtcactgt ctctgcag            48

<210> SEQ ID NO 11
<211> LENGTH: 52
<212> TYPE: DNA
<213> ORGANISM: mus musculus

<400> SEQUENCE: 11
tactatgcta tggactactg gggtcaagga acctcagtca ccgtctcctc ag        52

<210> SEQ ID NO 12
<211> LENGTH: 43
<212> TYPE: DNA
<213> ORGANISM: Artificial sequence
<220> FEATURE:
<223> OTHER INFORMATION: Consensus of mouse heavy chain J regions

<400> SEQUENCE: 12
tttgactact ggggccaagg gaccacggtc accgtctcct cag                 43

<210> SEQ ID NO 13
<211> LENGTH: 36
<212> TYPE: DNA
<213> ORGANISM: Homo sapiens

<400> SEQUENCE: 13
ggacgttcgg ccaagggacc aaggtggaaa tcaaac                         36

<210> SEQ ID NO 14
<211> LENGTH: 36
<212> TYPE: DNA
<213> ORGANISM: Homo sapiens

<400> SEQUENCE: 14
acacttttgg ccaggggacc aagctggaga tcaaac                         36

<210> SEQ ID NO 15
<211> LENGTH: 36
<212> TYPE: DNA
<213> ORGANISM: Homo sapiens

<400> SEQUENCE: 15
```

-continued tcactttcgg ccctgggacc aaagtggata tcaaac        36

<210> SEQ ID NO 16
<211> LENGTH: 36
<212> TYPE: DNA
<213> ORGANISM: Homo sapiens

<400> SEQUENCE: 16
tcactttcgg cggagggacc aaggtggaga tcaaac        36

<210> SEQ ID NO 17
<211> LENGTH: 36
<212> TYPE: DNA
<213> ORGANISM: Homo sapiens

<400> SEQUENCE: 17
tcaccttcgg ccaagggaca cgactggaga ttaaac        36

<210> SEQ ID NO 18
<211> LENGTH: 31
<212> TYPE: DNA
<213> ORGANISM: Artificial sequence
<220> FEATURE:
<223> OTHER INFORMATION: Consensus of human Kappa J regions

<400> SEQUENCE: 18
ttcggccaag ggaccaaggt ggagatcaaa c        31

<210> SEQ ID NO 19
<211> LENGTH: 37
<212> TYPE: DNA
<213> ORGANISM: mus musculus

<400> SEQUENCE: 19
tggacgttcg gtggaggcac caagctggaa atcaaac        37

<210> SEQ ID NO 20
<211> LENGTH: 37
<212> TYPE: DNA
<213> ORGANISM: mus musculus

<400> SEQUENCE: 20
tacacgttcg gaggggggac caagctggaa ataaaac        37

<210> SEQ ID NO 21
<211> LENGTH: 37
<212> TYPE: DNA
<213> ORGANISM: mus musculus

<400> SEQUENCE: 21
ttcacattca gtgatgggac cagactggaa ataaaac        37

<210> SEQ ID NO 22
<211> LENGTH: 37
<212> TYPE: DNA
<213> ORGANISM: mus musculus

<400> SEQUENCE: 22
ttcacgttcg gctcggggac aaagttggaa ataaaac        37

<210> SEQ ID NO 23
<211> LENGTH: 37
<212> TYPE: DNA
<213> ORGANISM: mus musculus

```
<400> SEQUENCE: 23
ctcacgttcg gtgctgggac caagctggag ctgaaac                                37

<210> SEQ ID NO 24
<211> LENGTH: 31
<212> TYPE: DNA
<213> ORGANISM: Artificial sequence
<220> FEATURE:
<223> OTHER INFORMATION: Consensus of mouse Kappa J regions

<400> SEQUENCE: 24
ttcggtgggg ggaccaagct ggaaataaaa c                                      31

<210> SEQ ID NO 25
<211> LENGTH: 19
<212> TYPE: DNA
<213> ORGANISM: Artificial sequence
<220> FEATURE:
<223> OTHER INFORMATION: consensus primer: UIG-MJK

<400> SEQUENCE: 25
gttttatttc cagcttggt                                                    19

<210> SEQ ID NO 26
<211> LENGTH: 37
<212> TYPE: DNA
<213> ORGANISM: Homo sapiens

<400> SEQUENCE: 26
cacatgtttg gcagcaagac ccagcccact gtcttag                                37

<210> SEQ ID NO 27
<211> LENGTH: 37
<212> TYPE: DNA
<213> ORGANISM: mus musculus

<400> SEQUENCE: 27
tgggtgttcg gtggaggaac caaactgact gtcctag                                37

<210> SEQ ID NO 28
<211> LENGTH: 37
<212> TYPE: DNA
<213> ORGANISM: mus musculus

<400> SEQUENCE: 28
tatgttttcg gcggtggaac caaggtcact gtcctag                                37

<210> SEQ ID NO 29
<211> LENGTH: 37
<212> TYPE: DNA
<213> ORGANISM: mus musculus

<400> SEQUENCE: 29
tttattttcg gcagtggaac caaggtcact gtcctag                                37

<210> SEQ ID NO 30
<211> LENGTH: 31
<212> TYPE: DNA
<213> ORGANISM: Artificial sequence
<220> FEATURE:
<223> OTHER INFORMATION: Consensus of mouse Lambda J regions

<400> SEQUENCE: 30
```
ttcggcggtg gaaccaaggt cactgtccta g                                   31

<210> SEQ ID NO 31
<211> LENGTH: 51
<212> TYPE: DNA
<213> ORGANISM: mus musculus

<400> SEQUENCE: 31
tactggtact tcgatgtctg gggcgcaggg accacggtca ccgtctcctc a             51

<210> SEQ ID NO 32
<211> LENGTH: 45
<212> TYPE: DNA
<213> ORGANISM: mus musculus

<400> SEQUENCE: 32
tactttgact actggggcca aggcaccact ctcacagtct cctca                   45

<210> SEQ ID NO 33
<211> LENGTH: 47
<212> TYPE: DNA
<213> ORGANISM: mus musculus

<400> SEQUENCE: 33
cctggtttgc ttactggggc caagggactc tggtcactgt ctctgca                 47

<210> SEQ ID NO 34
<211> LENGTH: 51
<212> TYPE: DNA
<213> ORGANISM: mus musculus

<400> SEQUENCE: 34
tactatgcta tggactactg gggtcaagga acctcagtca ccgtctcctc a             51

<210> SEQ ID NO 35
<211> LENGTH: 21
<212> TYPE: DNA
<213> ORGANISM: Artificial sequence
<220> FEATURE:
<223> OTHER INFORMATION: Consensus primer: UIGH

<400> SEQUENCE: 35
agggaccacg gtcaccgtct c                                              21

<210> SEQ ID NO 36
<211> LENGTH: 36
<212> TYPE: DNA
<213> ORGANISM: mus musculus

<400> SEQUENCE: 36
tggacgttcg gtggaggcac caagctggaa atcaaa                              36

<210> SEQ ID NO 37
<211> LENGTH: 36
<212> TYPE: DNA
<213> ORGANISM: mus musculus

<400> SEQUENCE: 37
tacacgttcg gaggggggac caagctggaa ataaaa                              36

<210> SEQ ID NO 38
<211> LENGTH: 36
<212> TYPE: DNA
<213> ORGANISM: mus musculus -continued

<400> SEQUENCE: 38
ttcacgttcg gctcggggac aaagttggaa ataaaa                                    36

<210> SEQ ID NO 39
<211> LENGTH: 36
<212> TYPE: DNA
<213> ORGANISM: mus musculus

<400> SEQUENCE: 39
ctcacgttcg gtgctgggac caagctggag ctgaaa                                    36

<210> SEQ ID NO 40
<211> LENGTH: 15
<212> TYPE: DNA
<213> ORGANISM: Artificial sequence
<220> FEATURE:
<223> OTHER INFORMATION: Consensus primer: UIGK

<400> SEQUENCE: 40
gggaccaagc ttgag                                                          15

<210> SEQ ID NO 41
<211> LENGTH: 43
<212> TYPE: DNA
<213> ORGANISM: Homo sapiens

<400> SEQUENCE: 41
ggtcaccgtc tcttcagcct ccaccaaggg cccatcggtc ttc                           43

<210> SEQ ID NO 42
<211> LENGTH: 48
<212> TYPE: DNA
<213> ORGANISM: Homo sapiens

<400> SEQUENCE: 42
gatcatctcc ctctcacttt cggcggaggg accaaggtgg agatgaaa                      48

<210> SEQ ID NO 43
<211> LENGTH: 459
<212> TYPE: DNA
<213> ORGANISM: Mus musculus
<220> FEATURE:
<221> NAME/KEY: CDS
<222> LOCATION: (40)..(459)

<400> SEQUENCE: 43
cgtacctctc tacagtccct gaagacactg actctaacc atg gga ttc agc agg            54
                                            Met Gly Phe Ser Arg
                                             1               5 atc ttt ctc ttc ctc ctg tca gta act aca ggt gtc cac tcc cag gct          102
Ile Phe Leu Phe Leu Leu Ser Val Thr Thr Gly Val His Ser Gln Ala
            10                  15                  20 tat cta cag cag tct ggg gct gag ctg gtg agg cct ggg gcc tca gtg          150
Tyr Leu Gln Gln Ser Gly Ala Glu Leu Val Arg Pro Gly Ala Ser Val
        25                  30                  35 aag atg tcc tgc aag gct tct ggc tac aca ttt acc agt tac aat atg          198
Lys Met Ser Cys Lys Ala Ser Gly Tyr Thr Phe Thr Ser Tyr Asn Met
    40                  45                  50 cac tgg gta aag cag aca cct aga cag ggc ctg gaa tgg att gga gct          246
His Trp Val Lys Gln Thr Pro Arg Gln Gly Leu Glu Trp Ile Gly Ala
55                  60                  65 att tat cca gga aat ggt gat act tcc tac aat cag aag ttc aag ggc          294

```
Ile Tyr Pro Gly Asn Gly Asp Thr Ser Tyr Asn Gln Lys Phe Lys Gly
 70                  75                  80                  85 aag gcc aca ctg act gta gac aaa tcc tcc agc aca gcc tac atg cag        342
Lys Ala Thr Leu Thr Val Asp Lys Ser Ser Ser Thr Ala Tyr Met Gln
                 90                  95                 100 ctc agc agc ctg aca tct gaa gac tct gcg gtc tat ttc tgt gca aga        390
Leu Ser Ser Leu Thr Ser Glu Asp Ser Ala Val Tyr Phe Cys Ala Arg
            105                 110                 115 gtg gtg tac tat agt aac tct tac tgg tac ttc gat gtc tgg ggc aca        438
Val Val Tyr Tyr Ser Asn Ser Tyr Trp Tyr Phe Asp Val Trp Gly Thr
        120                 125                 130 ggg acc acg gtc acc gtc tcg                                            459
Gly Thr Thr Val Thr Val Ser
    135                 140

<210> SEQ ID NO 44
<211> LENGTH: 140
<212> TYPE: PRT
<213> ORGANISM: Mus musculus

<400> SEQUENCE: 44

Met Gly Phe Ser Arg Ile Phe Leu Phe Leu Leu Ser Val Thr Thr Gly
1               5                  10                  15

Val His Ser Gln Ala Tyr Leu Gln Gln Ser Gly Ala Glu Leu Val Arg
            20                  25                  30

Pro Gly Ala Ser Val Lys Met Ser Cys Lys Ala Ser Gly Tyr Thr Phe
        35                  40                  45

Thr Ser Tyr Asn Met His Trp Val Lys Gln Thr Pro Arg Gln Gly Leu
    50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Val Asp Lys Ser Ser Ser
                85                  90                  95

Thr Ala Tyr Met Gln Leu Ser Ser Leu Thr Ser Glu Asp Ser Ala Val
            100                 105                 110

Tyr Phe Cys Ala Arg Val Val Tyr Tyr Ser Asn Ser Tyr Trp Tyr Phe
        115                 120                 125

Asp Val Trp Gly Thr Gly Thr Thr Val Thr Val Ser
    130                 135                 140

<210> SEQ ID NO 45
<211> LENGTH: 403
<212> TYPE: DNA
<213> ORGANISM: Mus musculus
<220> FEATURE:
<221> NAME/KEY: CDS
<222> LOCATION: (20)..(403)

<400> SEQUENCE: 45
ccccaaaatt caaagacaa atg gat ttt caa gtg cag att ttc agc ttc ctg        52
                    Met Asp Phe Gln Val Gln Ile Phe Ser Phe Leu
                     1               5                  10 cta atc agt gct tca gtc ata att gcc aga gga caa att gtt ctc tcc       100
Leu Ile Ser Ala Ser Val Ile Ile Ala Arg Gly Gln Ile Val Leu Ser
            15                  20                  25 cag tct cca gca atc ctg tct gca tct cca ggg gag aag gtc aca atg       148
Gln Ser Pro Ala Ile Leu Ser Ala Ser Pro Gly Glu Lys Val Thr Met
        30                  35                  40 act tgc agg gcc agc tca agt gta agt tac atg cac tgg tac cag cag       196
Thr Cys Arg Ala Ser Ser Ser Val Ser Tyr Met His Trp Tyr Gln Gln
```

```
                   45                  50                  55
aag cca gga tcc tcc ccc aaa ccc tgg att tat gcc cca tcc aac ctg     244
Lys Pro Gly Ser Ser Pro Lys Pro Trp Ile Tyr Ala Pro Ser Asn Leu
 60                  65                  70                  75 gct tct gga gtc cct gct cgc ttc agt ggc agt ggg tct ggg acc tct     292
Ala Ser Gly Val Pro Ala Arg Phe Ser Gly Ser Gly Ser Gly Thr Ser
                 80                  85                  90 tac tct ctc aca atc agc aga gtg gag gct gaa gat gct gcc act tat     340
Tyr Ser Leu Thr Ile Ser Arg Val Glu Ala Glu Asp Ala Ala Thr Tyr
             95                 100                 105 tac tgc cag cag tgg agt ttt aac cca ccc acg ttc ggt gct ggg acc     388
Tyr Cys Gln Gln Trp Ser Phe Asn Pro Pro Thr Phe Gly Ala Gly Thr
        110                 115                 120 aag ctg gag ctg aaa                                                 403
Lys Leu Glu Leu Lys
125
```

<210> SEQ ID NO 46
<211> LENGTH: 128
<212> TYPE: PRT
<213> ORGANISM: Mus musculus

<400> SEQUENCE: 46

```
Met Asp Phe Gln Val Gln Ile Phe Ser Phe Leu Leu Ile Ser Ala Ser
 1               5                  10                  15

Val Ile Ile Ala Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met His Trp Tyr Gln Gln Lys Pro Gly Ser Ser
    50                  55                  60

Pro Lys Pro Trp Ile Tyr Ala Pro Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Ser Phe Asn Pro Pro Thr Phe Gly Ala Gly Thr Lys Leu Glu Leu Lys
        115                 120                 125
```

<210> SEQ ID NO 47
<211> LENGTH: 12
<212> TYPE: DNA
<213> ORGANISM: Artificial sequence
<220> FEATURE:
<223> OTHER INFORMATION: 5' region of VH pH2-7(JH1)Bst EII Clone

<400> SEQUENCE: 47
gtcgacatgg ga                                                       12

<210> SEQ ID NO 48
<211> LENGTH: 24
<212> TYPE: DNA
<213> ORGANISM: Artificial sequence
<220> FEATURE:
<223> OTHER INFORMATION: Joint region of VH pH2-7(JH1)Bst EII Clone

<400> SEQUENCE: 48
acggtcaccg tctcttcagc ctcc                                          24

```
<210> SEQ ID NO 49
<211> LENGTH: 15
<212> TYPE: DNA
<213> ORGANISM: Artificial sequence
<220> FEATURE:
<223> OTHER INFORMATION: 5' region of Vk pL2-12 (Jk5) oligo(dT) clone

<400> SEQUENCE: 49
gtcgacaaaa tggat                                                    15

<210> SEQ ID NO 50
<211> LENGTH: 24
<212> TYPE: DNA
<213> ORGANISM: Artificial sequence
<220> FEATURE:
<223> OTHER INFORMATION: Joint region of Vk pL2-12 (Jk5) oligo(dT) clone

<400> SEQUENCE: 50
accaagcttg agatgaaacg aact                                          24
```

What is new and intended to be coveted by Letters Patent of the United States is:

1. A method for treating a B-cell disorder comprising administering to a patient an effective amount of an antibody molecule comprising two light chains and two heavy chains, wherein the antibody molecule comprises a variable region having specificity for a CD20 antigen bound by an antibody produced by hybridoma HB9303 as deposited withthe ATCC and a human constant region and wherein the antibody molecule has therapeutic activity in the treatment of B-cell disorders and is capable of mediating antibody-dependent cellular cytotoxicity or complement-dependent cytolysis.

2. The method of claim 1 wherein the antibody molecule is capable of mediating antibody-dependent cellular cytotoxicity.

3. The method of claim 1 wherein the antibody molecule is capable of mediating complement-dependent cytolysis.

4. The method of claim 1 wherein the antibody molecule is coupled to a drug, toxin, radioactive isotope, immunomodulator, or peptide effector.

5. The method of claim 4 wherein the toxin is ricin.

6. The method of claim 1 wherein the B-cell disorder comprises a B-cell malignancy.

7. The method of claim 6 wherein the B-cell malignancy comprises leukemia.

8. The method of claim 6 wherein the B-cell malignancy comprises lymphoma.

9. The method of claim 1 wherein the antibody molecule is produced by a eukaryotic host cell.

10. The method of claim 9 wherein the eukaryotic host cell is a CHO-K1 cell.

11. An antibody molecule useful in treating a B-cell disorder comprising two light chains and two heavy chains, wherein the antibody molecule comprises a human constant region and a variable region having specificity for a CD20 antigen bound by an antibody produced by hybridoma HB9303 as deposited with the ATCC and wherein the antibody molecule has therapeutic activity in the treatment of B-cell disorders and is capable of mediating antibody-dependent cellular cytotoxicity or complement-dependent cytolysis.

12. The antibody molecule of claim 11 wherein the antibody molecule is capable of mediating antibody-dependent cellular cytotoxicity.

13. The antibody molecule of claim 11 wherein the antibody molecule is capable of mediating complement-dependent cytolysis.

14. The antibody molecule of claim 11 wherein the antibody molecule is coupled to a drug, toxin, radioactive isotope, immunomodulator, or peptide effector.

15. The antibody molecule of claim 14 wherein the toxin is ricin.

16. The antibody molecule of claim 11 wherein the B-cell disorder comprises a B-cell malignancy.

17. The antibody molecule of claim 16 wherein the B-cell malignancy comprises leukemia.

18. The antibody molecule of claim 16 wherein the B-cell malignancy comprises lymphoma.

19. The antibody molecule of claim 11 wherein the antibody molecule is produced by a eukaryotic host cell.

20. The antibody molecule of claim 19 wherein the eukaryotic host cell is a CHO-K1 cell.

21. A therapeutic composition for the treatment of a Bell disorder comprising:
  a stabilizing reagent; and
  an antibody molecule comprising two light chains and two heavy chains, wherein the antibody molecule comprises a human constant region and a variable region having specificity for a CD20 antigen bound by an antibody produced by hybridoma HB9303 as deposited with the ATCC and wherein the antibody molecule has therapeutic activity in the treatment of B-cell disorders and is capable of mediating antibody-dependent cellular cytotoxicity or complement-dependent cytolysis.

22. The composition of claim 21 wherein the antibody molecule is capable of mediating antibody-dependent cellular cytotoxicity.

23. The composition of claim 21 wherein the antibody molecule is capable of mediating complement-dependent cytolysis.

24. The composition of claim 21 wherein the antibody molecule is coupled to a drug, toxin, radioactive isotope, immunomodulator, or peptide effector.

25. The composition of claim 24 wherein the toxin is ricin.

26. The composition of claim 21 wherein the B-cell disorder comprises a B-cell malignancy.

27. The composition of claim 26 wherein the B-cell malignancy comprises leukemia.

28. The composition of claim 26 wherein the B-cell malignancy comprises lymphoma.

29. The composition of claim 21 wherein the antibody molecule is produced by a eukaryotic host cell.

30. The composition of claim 29 wherein the eukaryotic host cell is a CHO-K1 cell.

* * * * *

UNITED STATES PATENT AND TRADEMARK OFFICE
CERTIFICATE OF CORRECTION

PATENT NO. : 6,652,852 B1
DATED : November 25, 2003
INVENTOR(S) : Robinson et al.

It is certified that error appears in the above-identified patent and that said Letters Patent is hereby corrected as shown below:

Column 37,
Line 30, replace "withthe" with -- with the --; and

Column 38,
Line 41, replace "Bell" with -- B-cell --.

Signed and Sealed this

Twenty-fourth Day of February, 2004

JON W. DUDAS
*Acting Director of the United States Patent and Trademark Office*